US010293562B2

(12) United States Patent
Jha et al.

(10) Patent No.: US 10,293,562 B2
(45) Date of Patent: May 21, 2019

(54) APPARATUS AND METHOD FOR MANUFACTURING FLEXIBLE PIPE

(71) Applicant: GE Oil & Gas UK Limited, Bristol (GB)

(72) Inventors: Vineet Jha, Newcastle (GB); Neville Dodds, Newcastle (GB); James Latto, Newcastle (GB); David Andrew Finch, Newcastle (GB)

(73) Assignee: GE OIL & GAS UK LIMITED, Bristol (GB)

( * ) Notice: Subject to any disclaimer, the term of this patent is extended or adjusted under 35 U.S.C. 154(b) by 0 days.

(21) Appl. No.: 15/533,900

(22) PCT Filed: Dec. 3, 2015

(86) PCT No.: PCT/GB2015/053712
§ 371 (c)(1),
(2) Date: Jun. 7, 2017

(87) PCT Pub. No.: WO2016/092270
PCT Pub. Date: Jun. 16, 2016

(65) Prior Publication Data
US 2017/0334156 A1 Nov. 23, 2017

(30) Foreign Application Priority Data
Dec. 8, 2014 (GB) .................... 1421797.0

(51) Int. Cl.
B32B 41/00 (2006.01)
B29D 23/00 (2006.01)
(Continued)

(52) U.S. Cl.
CPC ............ *B29D 23/001* (2013.01); *B29C 70/32* (2013.01); *G01N 29/041* (2013.01); *G01N 29/043* (2013.01); *G01N 2291/0231* (2013.01)

(58) Field of Classification Search
CPC .. B29D 23/001; G01N 29/043; G01N 29/041; G01N 2291/0231; B29C 70/32
(Continued)

(56) References Cited

U.S. PATENT DOCUMENTS
6,725,123 B1  4/2004 Denuell

FOREIGN PATENT DOCUMENTS
CN    1557628 A   12/2004
CN  101680591 A    3/2010
(Continued)

OTHER PUBLICATIONS
International Preliminary Report on Patentability for International Application No. PCT/GB2015/053712 dated Jun. 13, 2017.
(Continued)

*Primary Examiner* — Michael N Orlando
*Assistant Examiner* — Joshel Rivera
(74) *Attorney, Agent, or Firm* — Knobbe Martens Olson and Bear, LLP

(57) ABSTRACT

A method and apparatus for manufacturing a composite layer of a flexible pipe are disclosed. The apparatus comprises a layer inspection station comprising at least one sensor, located down stream of and in an in-line configuration with an extrusion station or pultrusion station or winding station or deposition station for providing a tubular composite layer over an underlying substantially cylindrical surface via a continuous process. The inspection station automatically and continuously determines if at least one parameter of the tubular composite layer satisfies a respective predetermined condition in at least one region of the tubular composite layer as the tubular composite layer is transported proximate to the inspection station and indicates in real time at least one of a type, size and/or location of a defect in the tubular composite layer.

19 Claims, 37 Drawing Sheets

Figure 1:
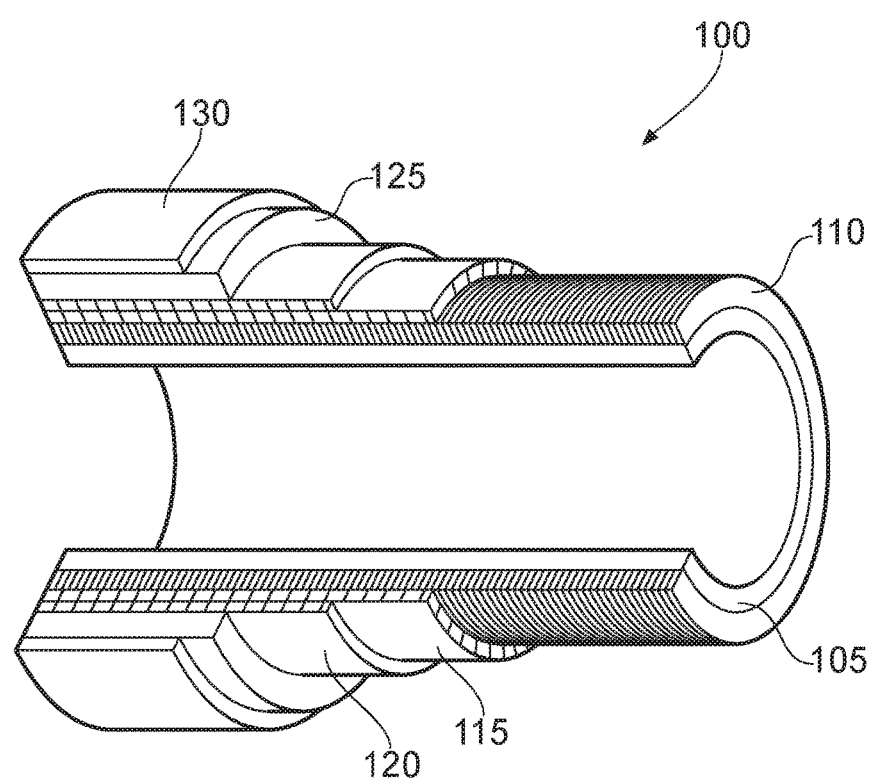

(51) Int. Cl.
*B29C 70/32* (2006.01)
*G01N 29/04* (2006.01)

(58) Field of Classification Search
USPC .......................... 156/64, 350, 351, 378, 379
See application file for complete search history.

(56) References Cited

FOREIGN PATENT DOCUMENTS

| CN | 101947851 A | 1/2011 |
|---|---|---|
| CN | 202846880 | 4/2013 |
| DE | 102009000938 | 5/2015 |
| EP | 0556635 | 8/1993 |
| JP | H03-102255 | 4/1991 |
| JP | H07-260751 | 10/1995 |
| JP | H07108588 | 11/1995 |
| JP | H10202724 | 8/1998 |
| WO | WO 2005/001466 | 6/2005 |
| WO | WO 2012/118378 | 9/2012 |

OTHER PUBLICATIONS

International Search Report and Written Opinion for International Application No. PCT/GB2015/053712 dated Mar. 7, 2016.

APPARATUS AND METHOD FOR MANUFACTURING FLEXIBLE PIPE

The present invention relates to a method and apparatus for manufacturing a composite layer for a flexible pipe. In particular, but not exclusively, the present invention relates to the manufacture of flexible pipe body via a continuous in-line process during which an inspection station provides an indication in real time of a type, size and/or location of any defect in a tubular composite layer of the pipe body so the defect can be corrected as part of the continuous process.

Traditionally flexible pipe is utilised to transport production fluids, such as oil and/or gas and/or water, from one location to another. Flexible pipe is particularly useful in connecting a sub-sea location (which may be deep underwater, say 1000 meters or more) to a sea level location. The pipe may have an internal diameter of typically up to around 0.6 meters (e.g. diameters may range from 0.05 m up to 0.6 m). Flexible pipe is generally formed as an assembly of flexible pipe body and one or more end fittings. The pipe body is typically formed as a combination of layered materials that form a pressure-containing conduit. The pipe structure allows large deflections without causing bending stresses that impair the pipe's functionality over its lifetime. There are different types of flexible pipe such as unbonded flexible pipe which is manufactured in accordance with API 17J or composite type flexible pipe or the like. The pipe body is generally built up as a combined structure including polymer layers and/or composite layers and/or metallic layers. For example, pipe body may include polymer and metal layers, or polymer and composite layers, or polymer, metal and composite layers. Depending upon the layers of the flexible pipe used and the type of flexible pipe some of the pipe layers may be bonded together or remain unbonded.

Some flexible pipe has been used for deep water (less than 3,300 feet (1,005.84 meters)) and ultra-deep water (greater than 3,300 feet) developments. It is the increasing demand for oil which is causing exploration to occur at greater and greater depths (for example in excess of 8202 feet (2500 meters)) where environmental factors are more extreme. For example in such deep and ultra-deep water environments ocean floor temperature increases the risk of production fluids cooling to a temperature that may lead to pipe blockage. In practice flexible pipe conventionally is designed to perform at operating temperatures of −30° C. to +130° C. Increased depths also increase the pressure associated with the environment in which the flexible pipe must operate. For example, a flexible pipe may be required to operate with external pressures ranging from 0.1 MPa to 30 MPa acting on the pipe. Equally, transporting oil, gas or water may well give rise to high pressures acting on the flexible pipe from within, for example with internal pressures ranging from zero to 140 MPa from bore fluid acting on the pipe. As a result the need for high levels of performance from the pressure armour and tensile armour layers of the flexible pipe body is increased. It is noted for the sake of completeness that flexible pipe may also be used for shallow water applications (for example less than around 500 meters depth) or even for shore (overland) applications.

Regardless of the type of flexible pipe body being manufactured, whenever a composite layer of flexible pipe body is to be manufactured defects can occur in the manufacturing step in which the composite layer is manufactured. For example voids caused by lack of fusion between successive windings of a tape and/or between adjacent layers or local regions of porosity caused by deficiencies in raw materials used can result in a composite layer containing one or more defects in one or more regions. Conventionally if not detected these defects can cause failure in any flexible pipe ultimately incorporating such layers. Conventional solutions can involve time consuming and thus costly after the event analysis and remedial work.

During manufacturing of flexible pipe body various layers of pipe body are manufactured via a range of processing steps. For example polymer layers can be extruded or layers can be formed by consolidating wound tape or layers of polymer material can be pultruded or deposited. Regardless of a manufacturing technique used, it is known that on occasion maintaining a desired shape in any cross section of the layer can be problematical. For example the roundness or ovality of a cross section of a layer should be maintained within predetermined desired limits. Ideally a cross section of a tubular layer should be perfectly circular. In practice according to conventional techniques some tubular layers have been susceptible to sagging which has led to an oval cross section being adopted over time. This can cause a problem when subsequent layers are manufactured over non-circular layers with a net result being that an end product, i.e. the flexible pipe body, does not have a desired shape.

It is an aim of the present invention to at least partly mitigate the above mentioned problems.

It is an aim of certain embodiments of the present invention to provide an apparatus and a method for manufacturing a composite layer as part of a process of making flexible pipe body.

It is an aim of certain embodiments of the present invention to provide a method and apparatus for manufacturing a tubular composite layer for an unbonded flexible pipe or for a bonded flexible pipe.

It is an aim of certain embodiments of the present invention to provide an inspection station which can be disposed in an in-line configuration and which can automatically and continuously indicate in real time at least one of a type, size and/or location of any defect in a tubular composite layer.

It is an aim of certain embodiments of the present invention to provide flexible pipe body, including at least one tubular composite layer, via an in-line continuous process in which one or more defects are automatically detected at an inspection station and an output from that inspection station is used in real time by a downstream in-line repair station to wholly or at least partially correct any defect in a single uni-directional production run.

It is an aim of certain embodiments of the present invention to continually adjust or correct a roundness or degree of ovality of a tubular composite layer as it is manufactured or as an initial/base tubular layer it is introduced into a manufacturing node where a further tubular composite layer is to be manufactured over the initial/base layer so as to produce an end product having a desired degree of ovality.

It is an aim of certain embodiments of the present invention to provide an inspection station for inspecting one or more layers of a flexible pipe as flexible pipe body is manufactured using a non-destructive testing (NDT) inspection technique.

It is an aim of certain embodiments of the present invention to provide a continuous production methodology for providing a composite layer including at least two component parts via an extrusion or winding or deposition process and being able to constantly monitor the generated layer to identify and indicate defects and/or take remedial action to wholly or partially correct the defects.

According to a first aspect of the present invention there is provided apparatus for manufacturing a composite layer of a flexible pipe, comprising:

a layer inspection station comprising at least one sensor, located downstream of and in an in-line configuration with an extrusion station or pultrusion station or winding station or deposition station for providing a tubular composite layer over an underlying substantially cylindrical surface via a continuous process; wherein the inspection station automatically and continuously determines if at least one parameter of the tubular composite layer satisfies a respective predetermined condition in at least one region of the tubular composite layer as the tubular composite layer is transported proximate to the inspection station and indicates in real time at least one of a type, size and/or location of a defect in the tubular composite layer.

Aptly the inspection station is downstream of, and in-line with, a winding station that comprises a winding carousel for continuously winding at least one tape element helically around the underlying cylindrical surface as a tubular element comprising the cylindrical surface is transported in a first direction of travel.

Aptly the apparatus further comprises a tape consolidation station downstream of, and in an in-line configuration with, the winding carousel for consolidating wound tape into a continuous composite layer that comprises said tubular composite layer.

Aptly the inspection station is located within 100 linear pipe meters of a touch down position where extruded material contacts the underlying cylindrical surface or where tape is wound onto the cylindrical surface respectively.

Aptly the inspection station provides non-destructive testing of the tubular composite layer.

Aptly the at least one sensor comprises at least one ultra-sonic sensor.

Aptly the at least one sensor indicates surface and sub-surface defects in the tubular composite layer.

Aptly the at least one sensor of the inspection station comprises a plurality of sensors disposed in a spaced apart relationship circumferentially around an outer surface of the tubular composite layer at a common location with respect to a longitudinal axis associated with a travel path of the tubular composite layer.

Aptly an output from each sensor is connected to an analysis unit via a multiplexor element for providing real-time monitoring of the at least one parameter at multiple regions of the tubular composite layer.

Aptly the at least one sensor comprises at least one phased array.

Aptly the apparatus further comprises a repair station comprising at least one heater member and/or pressure applicator located downstream of, and in an in-line configuration with, the inspection station for selectively applying a repair cycle by applying a desired temperature and/or pressure at said at least one region.

Aptly the repair station selectively heats the at least one tubular composite layer region to about around 120° C. to 250° C.

Aptly the tubular composite layer region is heated to about around 180° C. to 220° C.

Aptly the repair station selectively applies a pressure of about around 0.5 to 4 MPa via the heating member and/or pressure applicator to the at least one tubular composite layer region.

Aptly the repair station selectively applies the desired temperature and/or pressure for about around 0.5 to 60 seconds.

Aptly the temperature and/or pressure is applied for about around 1 to 2 seconds.

Aptly the repair station comprises at least one heater element.

Aptly the heater element comprises at least one of an infrared heater or induction heater or conductive heater or resistive heater.

Aptly the repair station comprises at least one cooler element which optionally comprises a fan element.

Aptly the repair station comprises at least one pressure applying member having an abutment surface having a shape at least substantially corresponding to a shape of an outer surface of the tubular composite layer or that is convex or concave.

Aptly the apparatus further comprises at least one tape spool that provides windable tape to the winding carousel for winding over the tubular element.

Aptly the apparatus further comprises a consolidation station located downstream of and in an in-line configuration with the winding station and upstream of, and in an in-line configuration with, the inspection station.

Aptly the apparatus further comprises a tape joining station that selectively joins juxtaposed ends of provided lengths of tape; wherein the joined lengths of tape provide a windable tape for the winding carousel having a length of more than 500 m.

Aptly the windable tape has a length of more than 1 km.

Aptly the tape joining station comprises a raw material spool and a tape storage spool.

Aptly the tape joining station further comprises at least one heated plate; and the juxtaposed ends of the lengths of tape are selectively locatable proximate to the heating plate and an opposed surface.

Aptly the apparatus further comprises at least one supply reel for the lengths of tape;

a first and further clamp member;

a joining press between the first and further clamp member; and a storage spool.

Aptly at least one of the supply reel or storage spool is driven.

Aptly the storage spool has a rim that provides a channel for engaging with a lifting beam.

Aptly the apparatus further comprises a re-rounder station downstream of the extrusion station or winding station.

Aptly the re-rounder station comprises at least one pressurised roller element that is selectively urgeable against an outer surface of the tubular composite layer.

Aptly each roller element has an outer surface that comprises an arcuate surface.

Aptly the cylindrical surface and surrounding tubular composite layer have a linear speed of transportation in a first direction of travel comprising a production direction of at least 0.25 m/min.

Aptly the tubular composite layer has a substantially circular cross section with an inner diameter of at least 3 inches.

Aptly the circular cross section has an inner diameter of at least about around 8 inches.

According to a second aspect of the present invention there is provided a method of manufacturing a composite layer of a flexible pipe, comprising the steps of:

via at least one sensor at a layer inspection station downstream of, and in an in-line configuration with, an extrusion station or pultrusion station or winding station or deposition station, automatically and continuously determining if at least one parameter of a tubular composite layer satisfies a respective predetermined condition in at least one region of the tubular composite layer and indicating in real time at least one of a type, size and/or location of a defect in the tubular composite layer.

Aptly the method further comprises transporting a tubular element comprising a substantially cylindrical outer surface in a first direction of travel comprising a direction of production; and via a winding carousel upstream of the layer inspection station, continuously winding at least one tape element helically around the substantially cylindrical surface of the tubular element.

Aptly the method further comprises consolidating wound tape via a tape consolidation station downstream of, and in an in-line configuration with, the winding carousel thereby providing a tubular composite layer.

Aptly the method further comprises simultaneously consolidating the tubular composite layer with the underlying tubular element thereby providing a fully bonded interface.

Aptly the method further comprises determining if said parameter satisfies said condition via a non-destructive testing method.

Aptly the step of determining if said parameter satisfies a predetermined condition comprises determining where there is a void space in the tubular composite layer or between the tubular composite layer and a further layer.

Aptly the step of determining if said parameter satisfies a predetermined condition comprises determining where there is a region of local porosity in the tubular composite layer.

Aptly the step of determining if said parameter satisfies a predetermined condition comprises determining where resin matrix micro cracking has occurred in the tubular composite layer.

Aptly the method further comprises, via each sensor, repeatedly providing at least one ultra-sonic pulse into the tubular composite layer at a respective probe region and detecting a respective reflected pulse.

Aptly the method further comprises providing the repeated pulses at a fixed location as the tubular composite layer is transported past the fixed location.

Aptly the method further comprises determining if said at least one parameter satisfies a respective predetermined condition in real time as the tubular composite layer is manufactured via a continuous process.

Aptly the method further comprises displaying on a display of a user interface, a representation of the tubular composite layer; and illustrating each said at least one region where said at least one parameter satisfied the predetermined condition on the display.

Aptly the method further comprises simultaneously determining if the at least one parameter satisfies said a respective predetermined parameter at a plurality of locations circumferentially spaced apart around a circumference of the tubular composite layer.

Aptly the method further comprises responsive to detection of a defect in at least one region via the inspection station, via a repair station located downstream of, and in an in-line configuration with the inspection station, selectively applying a desired fixed or varying temperature and/or pressure to a defective region as the defective region is transported proximate to the repair station.

Aptly the method further comprises via a re-rounding station, re-rounding a tubular composite layer downstream of the extrusion station or winding station or deposition station.

Aptly the method further comprises, via the re-rounding station, exerting a substantially uniform pressure circumferentially to the tubular composite layer or an underlying liner or barrier layer to thereby provide a pre-set ovality tolerance.

Aptly the method further comprises advancing the tubular element through a plurality of spring loaded or pneumatic or hydraulically actuated rollers each having a curved outer running surface.

Aptly the method further comprises unwinding a continuous length of tape from a storage spool;

via a winding carousel, directing the unwound length of tape along a set path to a touchdown point on the substantially cylindrical surface; and determining tape tension and/or tape angle and/or tape pre heat temperature and/or tape gap and/or heat consolidation temperature and/or underlying layer pre heat temperature and/or consolidation force.

Aptly the method further comprises providing a desired tape angle via a grooved roller having at least one inset region that guides tape as it moves towards a touch down point.

Aptly the method further comprises, via a tape break sensor disposed proximate to a tape path, generating an audio and/or visual cue if a tape break event occurs.

Aptly the method further comprises pre-heating tape and/or an immediately underlying layer over which the tape is wound to a least a melting point associated with one of the tape material or tape matrix and/or material of the underlying layer.

Aptly the method further comprises continuously transporting the tubular composite layer at a line speed of about around 0.5 to 1.0 m per min.

Aptly the method further comprises consolidating wound tape windings to adjacent windings by urging respective radially outer surfaces of adjacent windings radially inwardly.

Aptly the method further comprises continually cooling an outer surface of a consolidation roller as it urges the adjacent windings radially inwardly.

Aptly the method further comprises maintaining a line tension on the tubular composite layer between a pre-set minimum and maximum tension as the tubular composite layer is manufactured.

According to a third aspect of the present invention there is provided apparatus constructed and arranged substantially as herein after described with reference to the accompanying drawings.

According to a fourth aspect of the present invention there is provided a method substantially as herein after described with reference to the accompanying drawings.

Certain embodiments of the present invention provide a method and apparatus for manufacturing a composite layer for a flexible pipe using an in-line continuous production process which includes an ability to continuously identify defective regions in a generated composite layer.

Certain embodiments of the present invention provide apparatus for manufacturing a composite layer for a flexible pipe in which a layer inspection station which includes at least one sensor can be located in an in-line configuration downstream of an extrusion station or winding station or deposition station and can be used to continually and automatically indicate, in real time, at least one characteristic of one or more defects which may be present in the manufactured composite layer.

Certain embodiments of the present invention provide a layer inspection station downstream of a winding station and tape consolidation station which can, in real time, identify defects in a composite layer manufactured as part of the process of manufacturing flexible pipe body.

Certain embodiments of the present invention can be utilised to make a composite layer for an unbonded or bonded flexible pipe.

Figure 2:
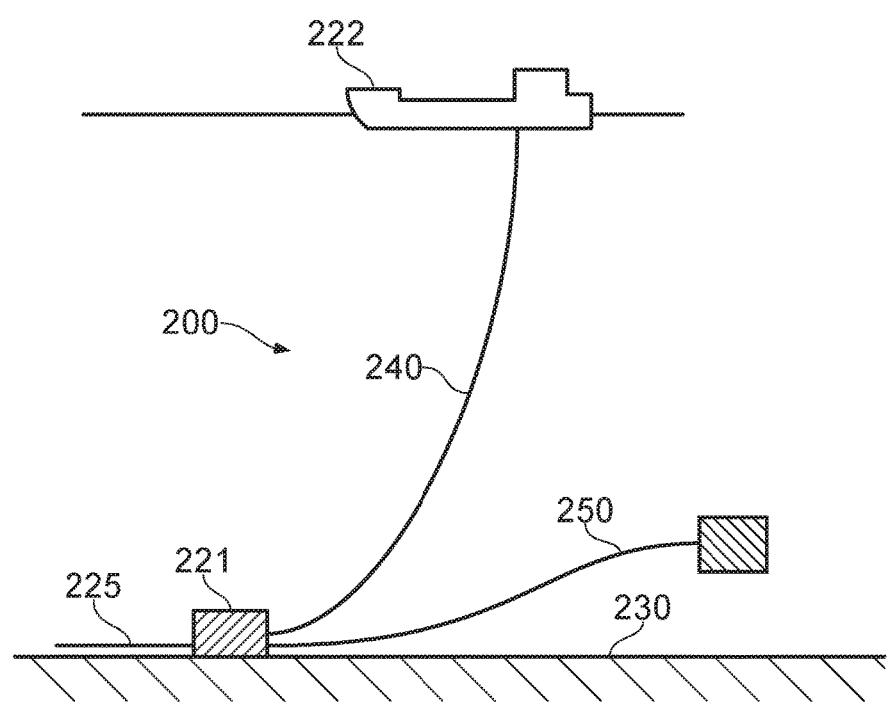
Figure 3:
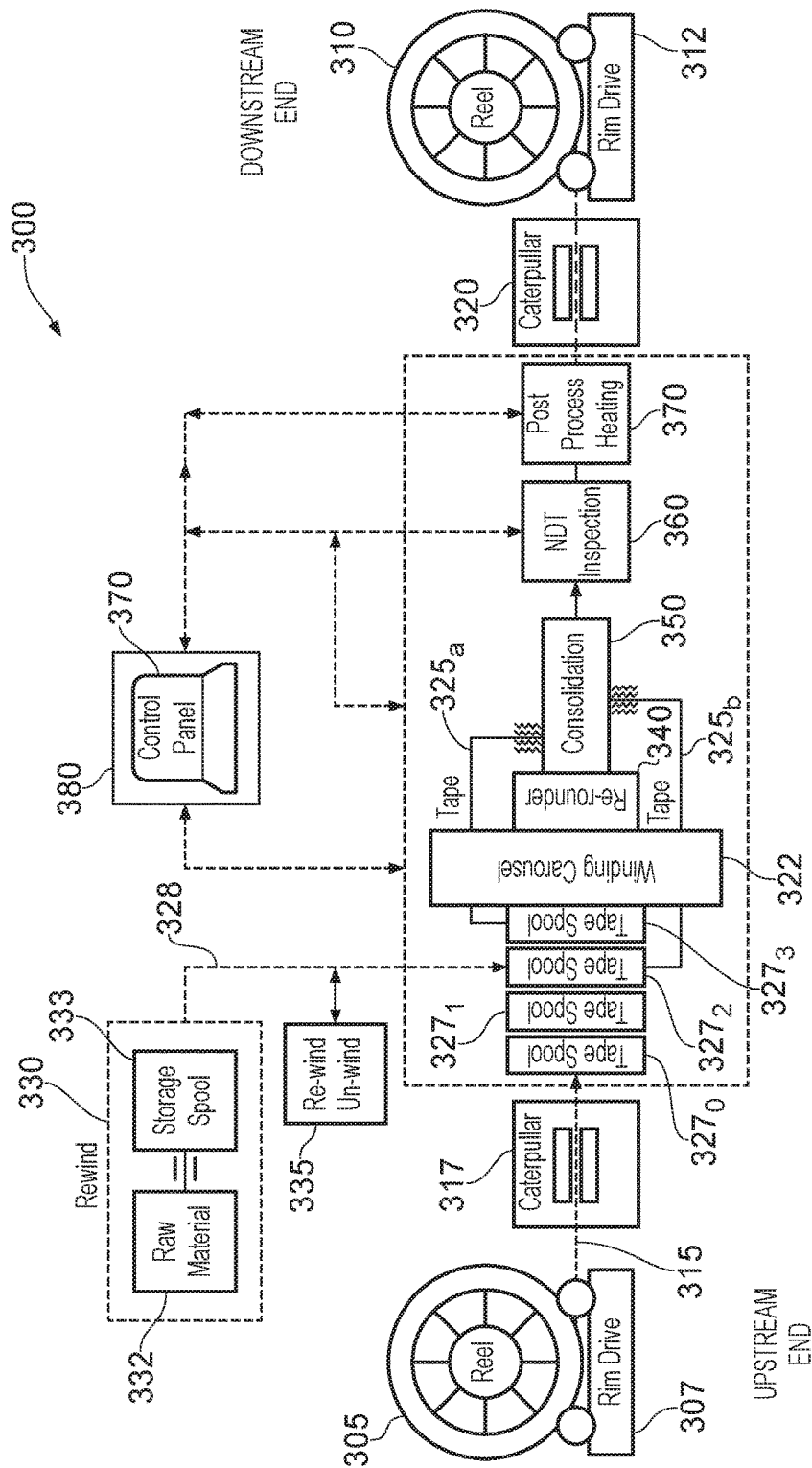
Figure 4:
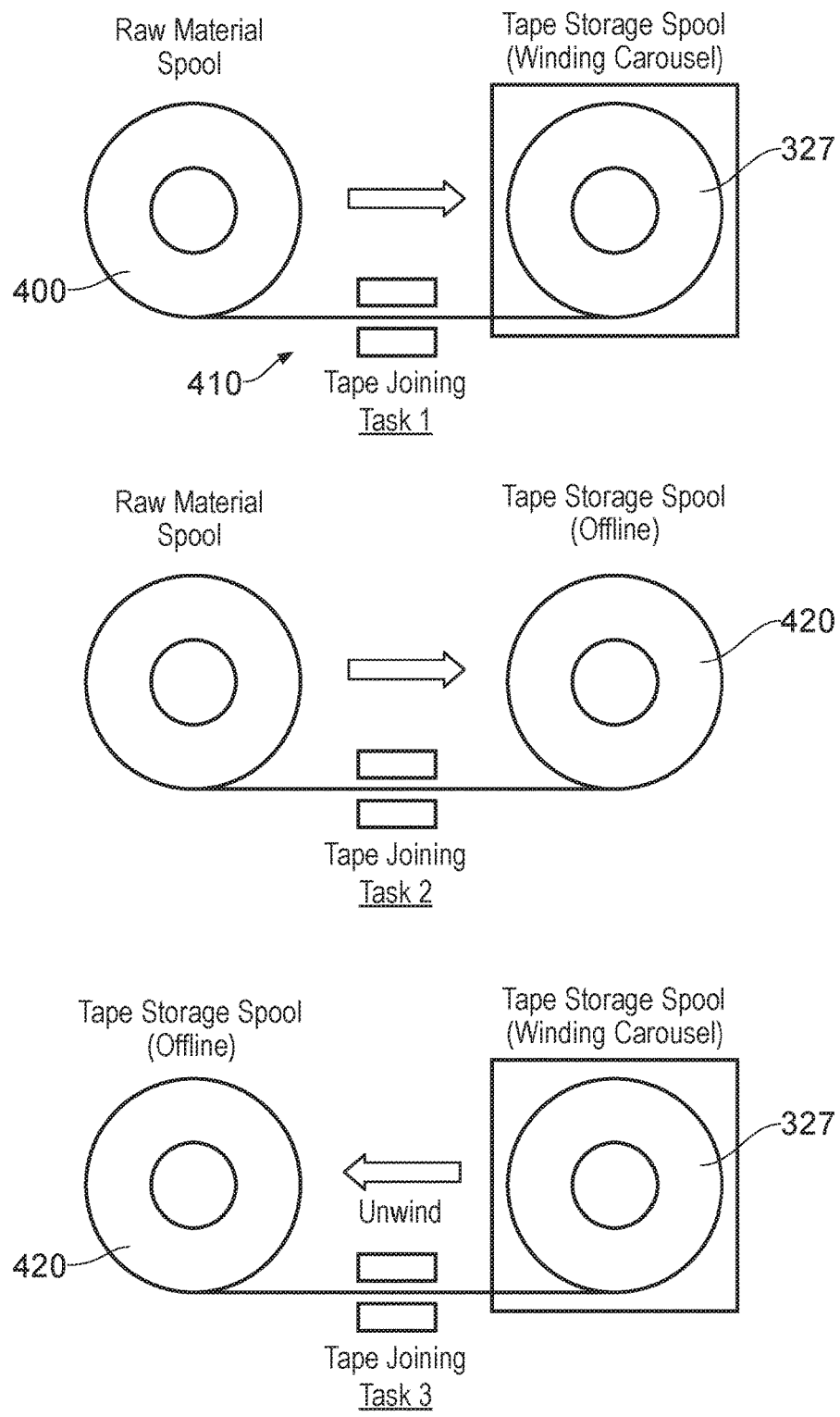
Figure 5:
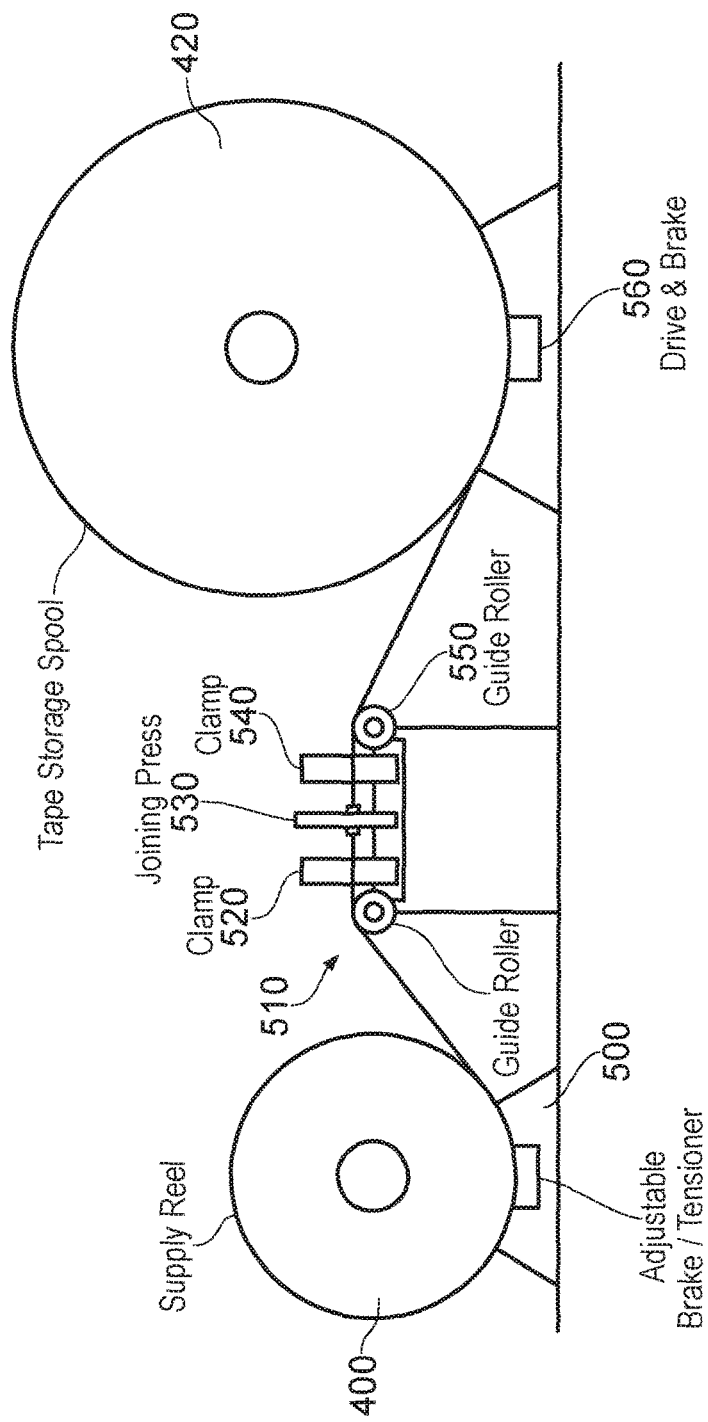
Figure 6:
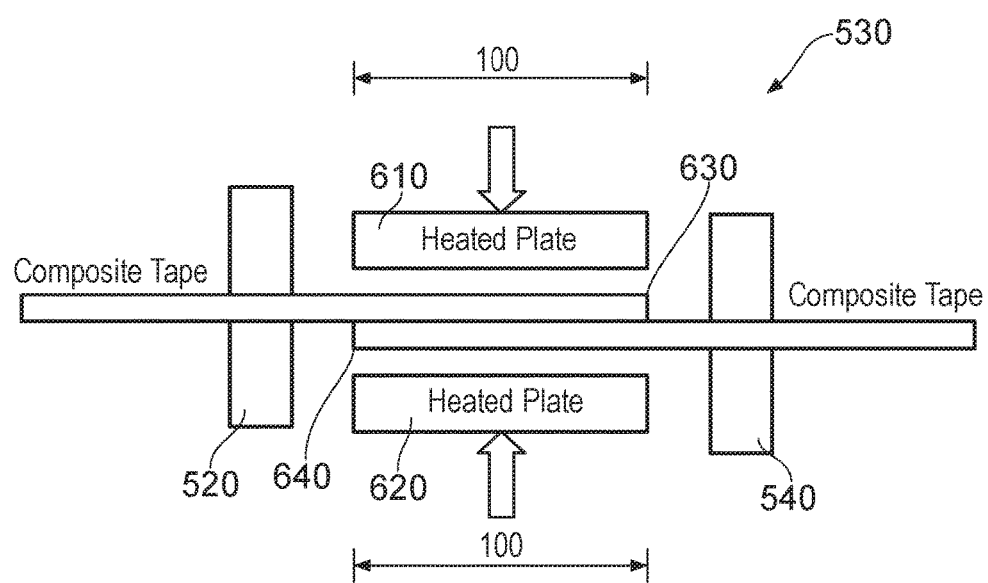
Figure 7:
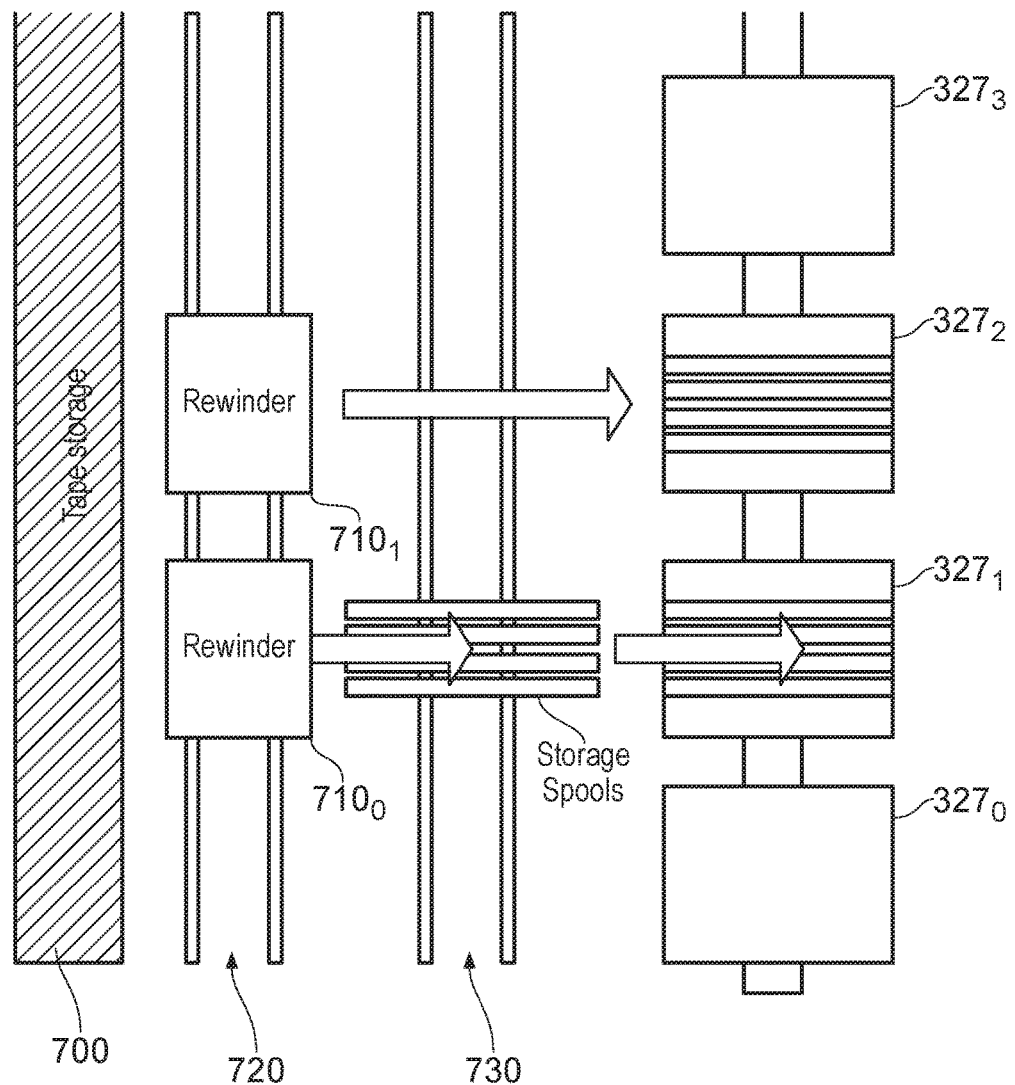
Figure 8:
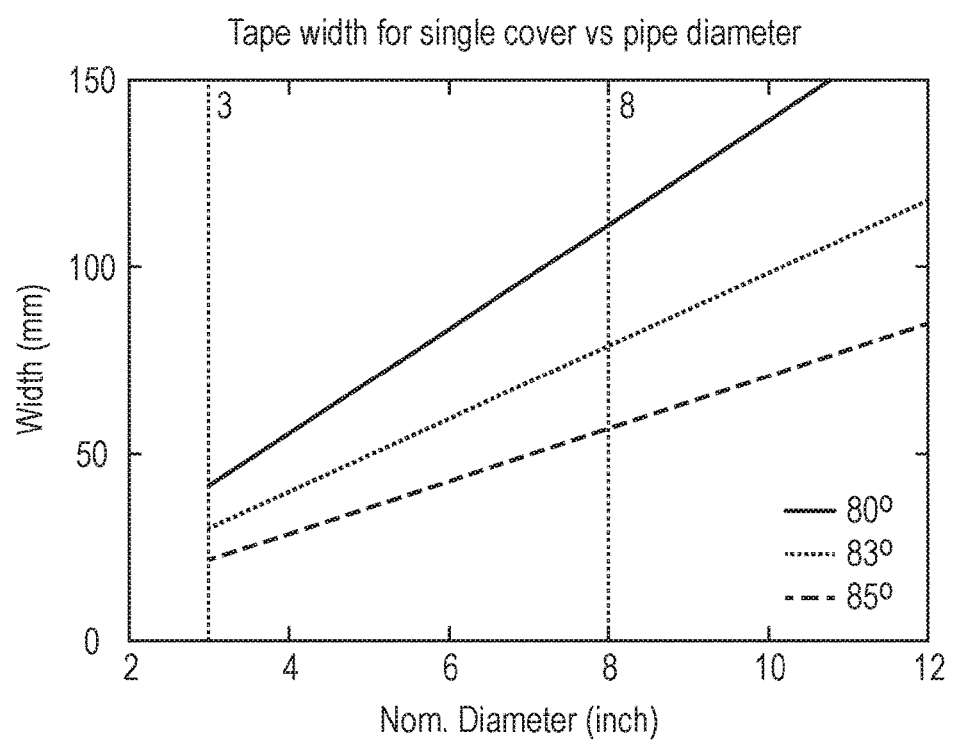
Figure 9:
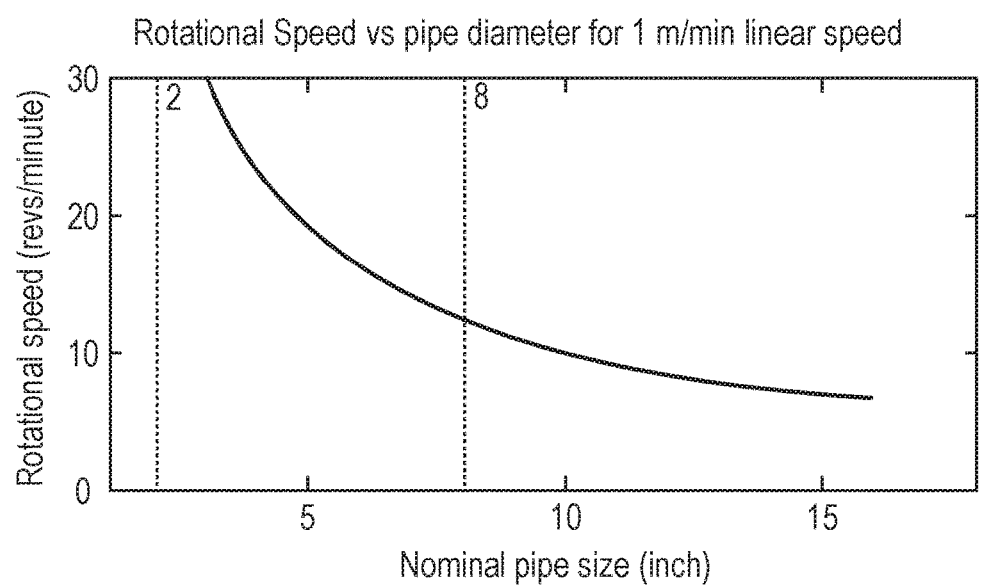
Figures 10, 11:
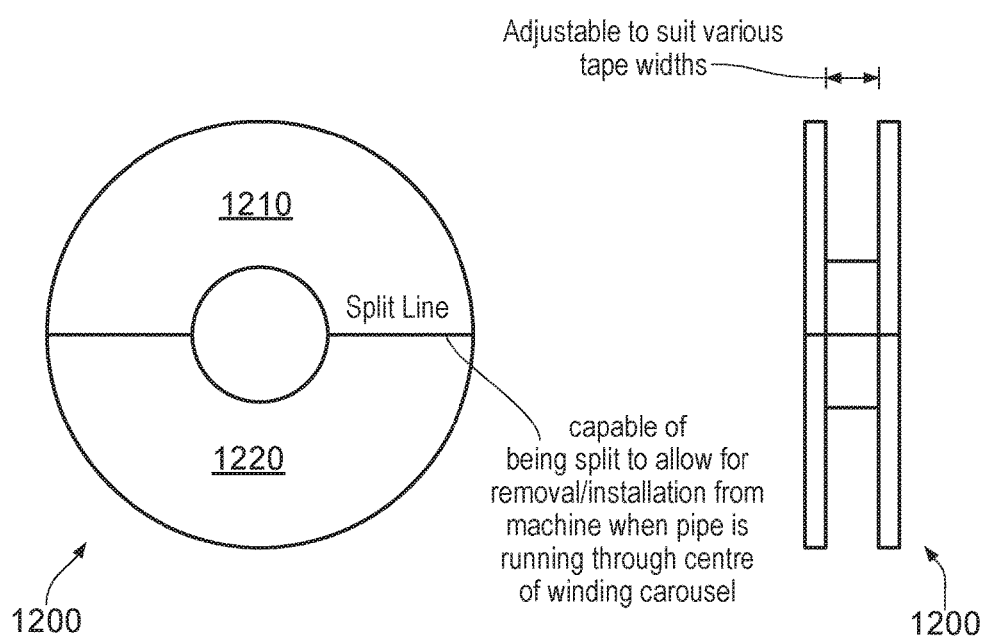
Figure 12:
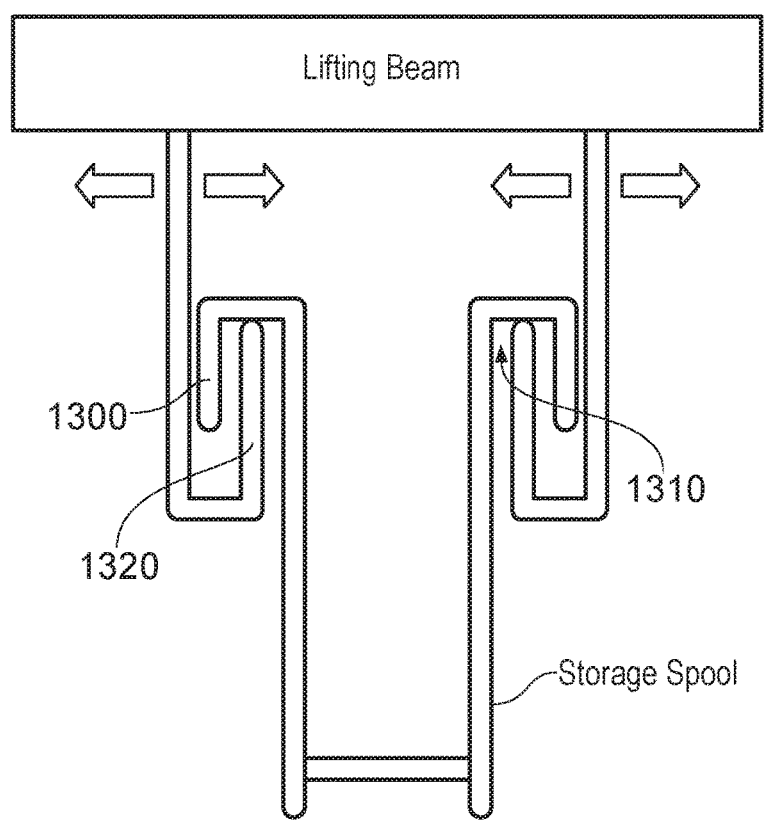
Figure 13:
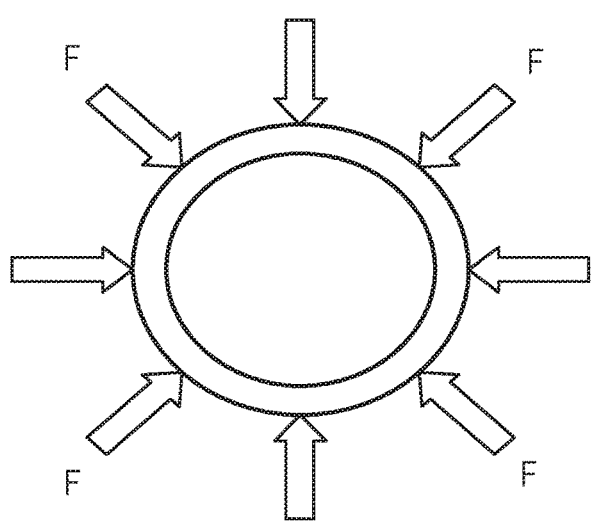
Figure 14:
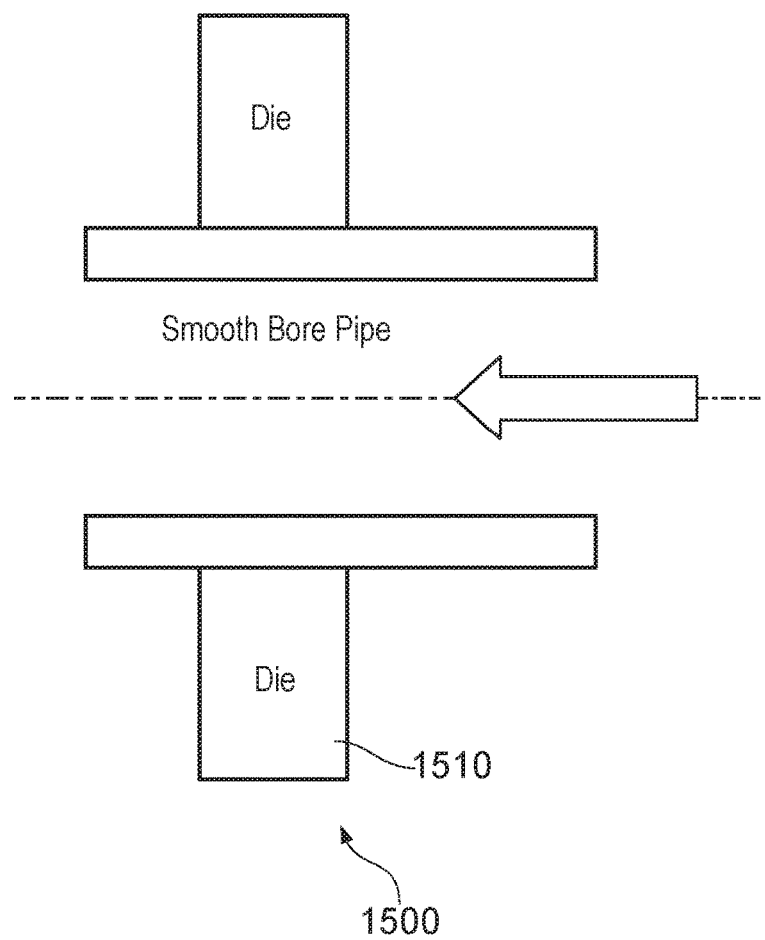
Figure 15:
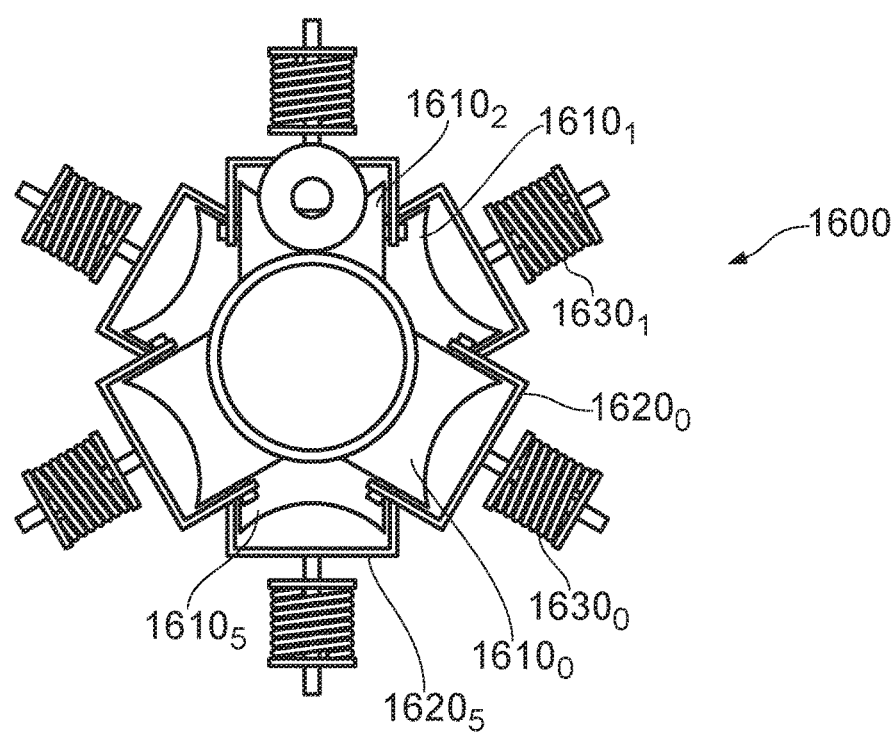
Figure 16:
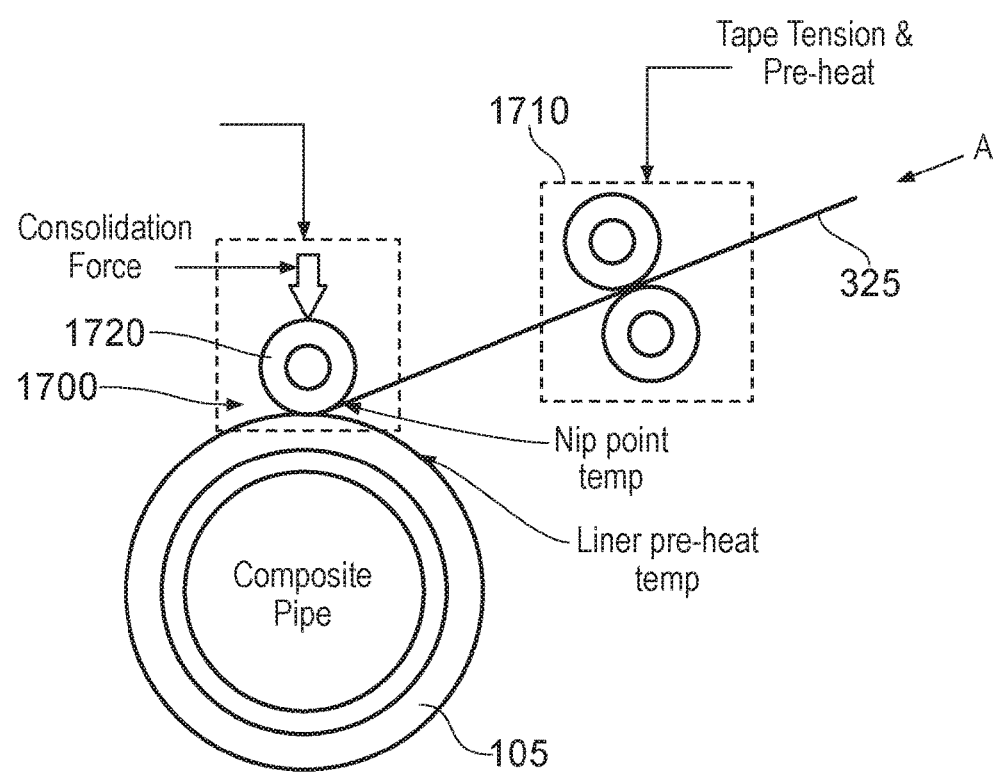
Figure 17:
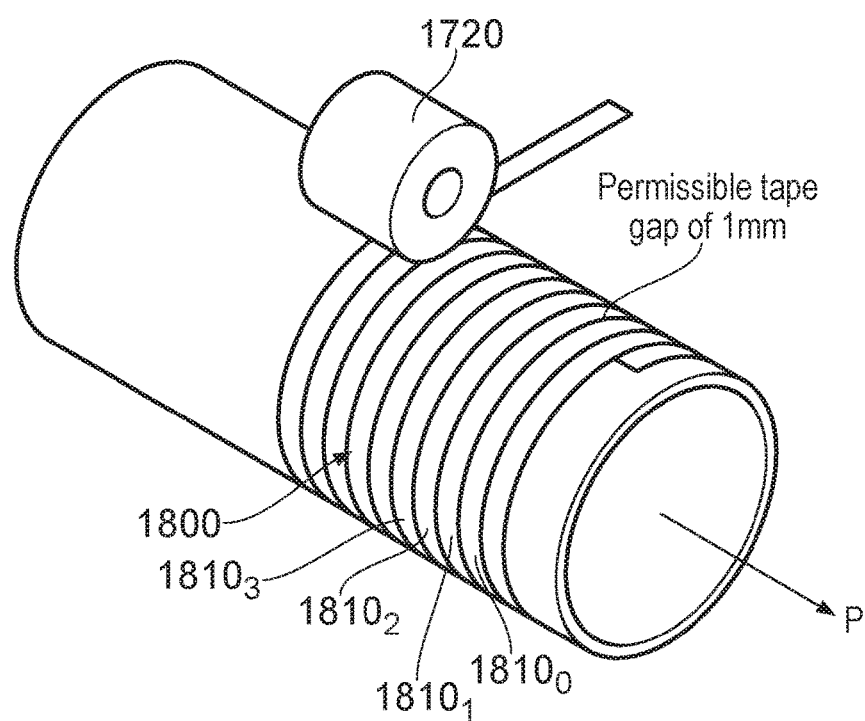
Figure 18:
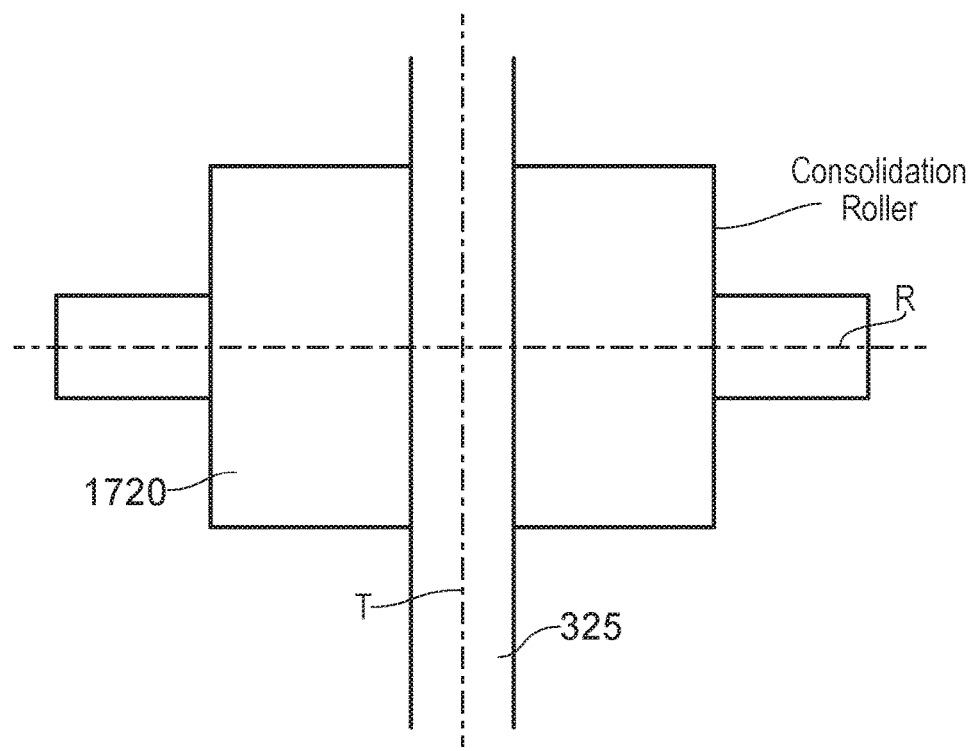
Figure 19:
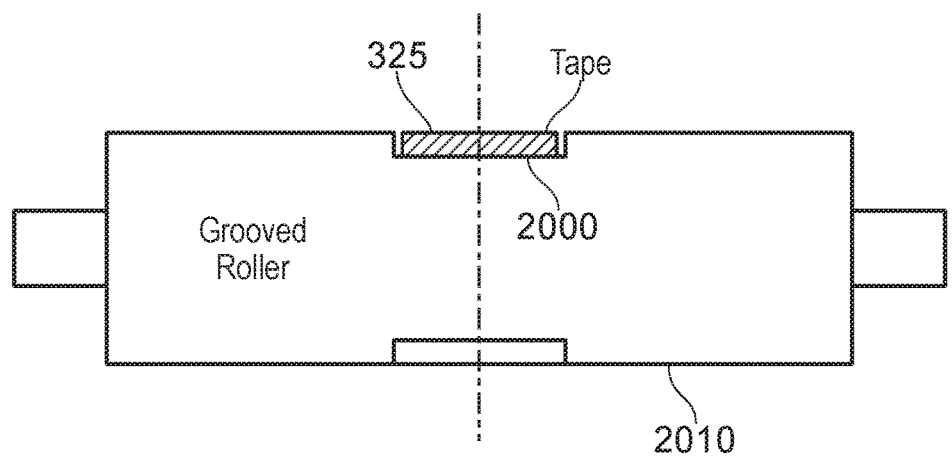
Figure 20:
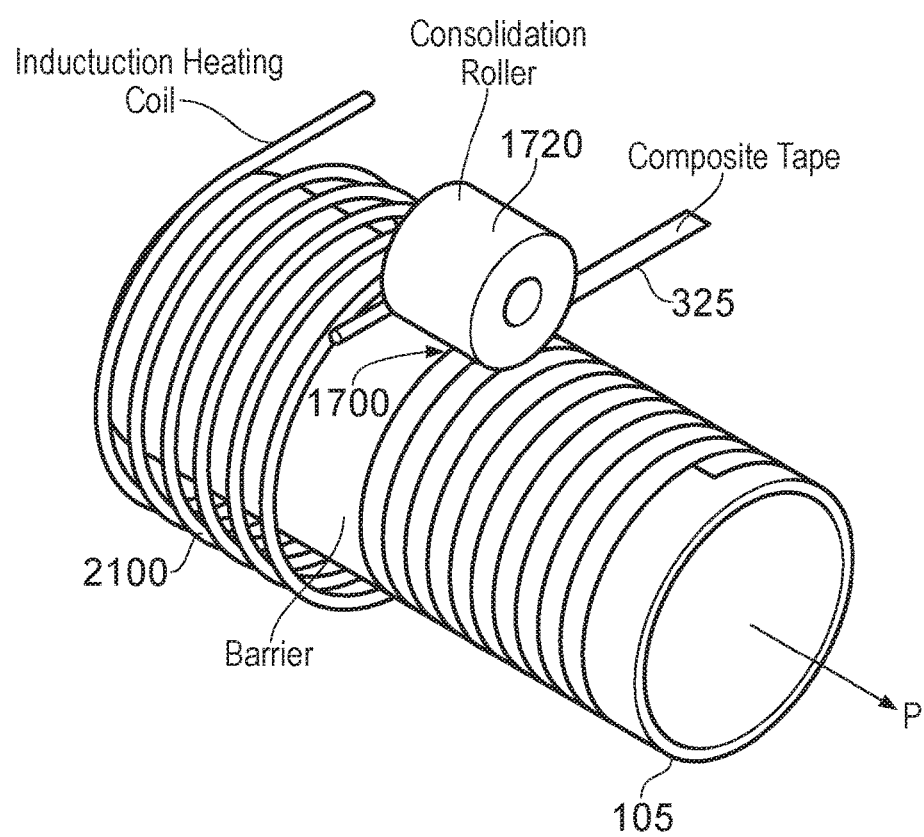
Figure 21:
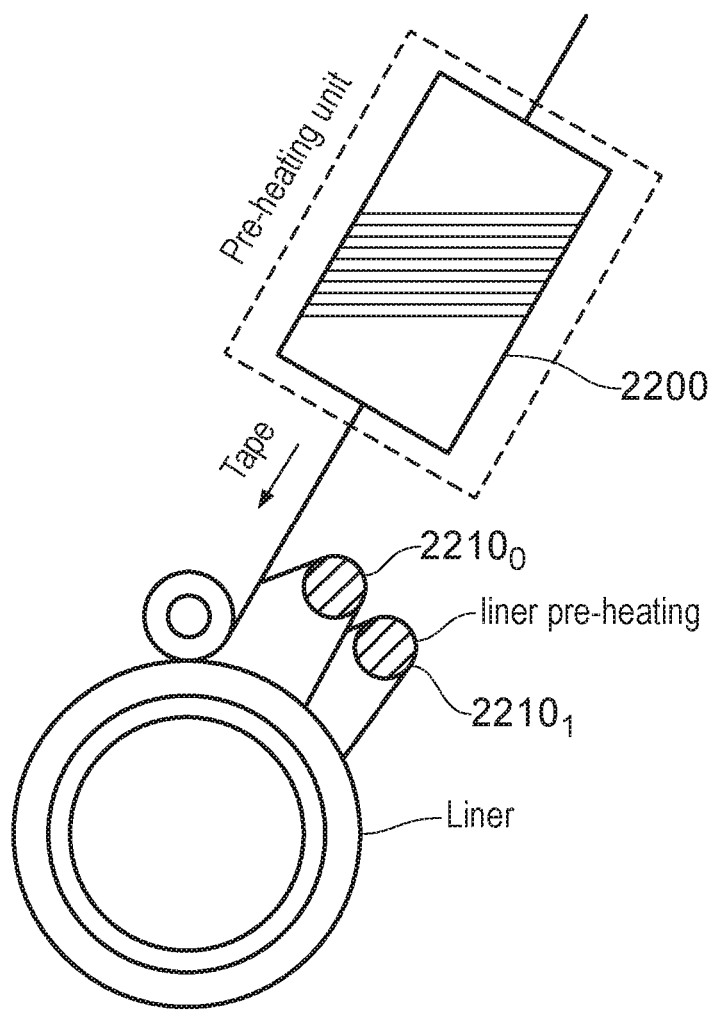
Figure 22:
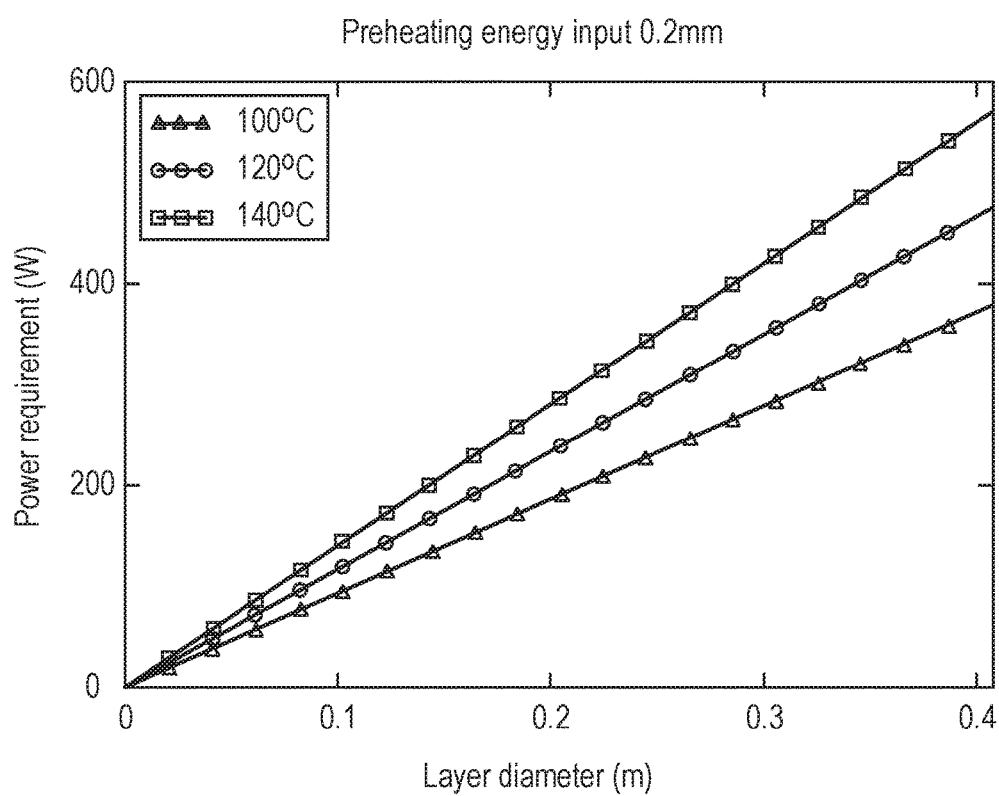
Figure 23:
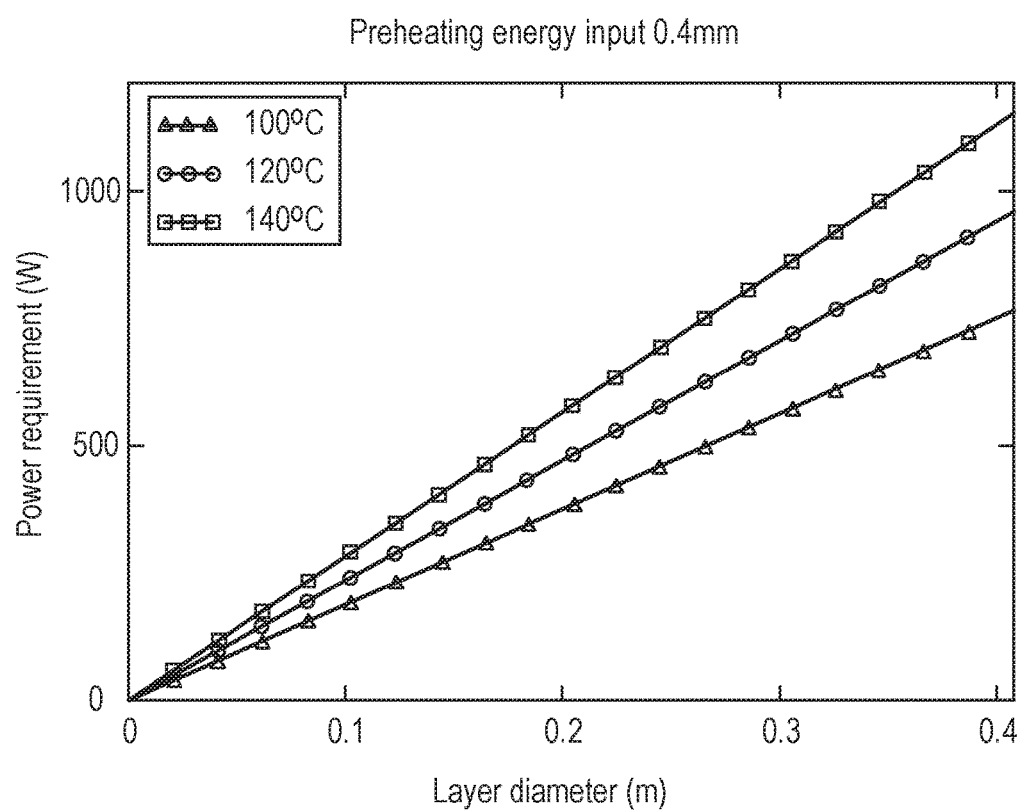
Figure 24:
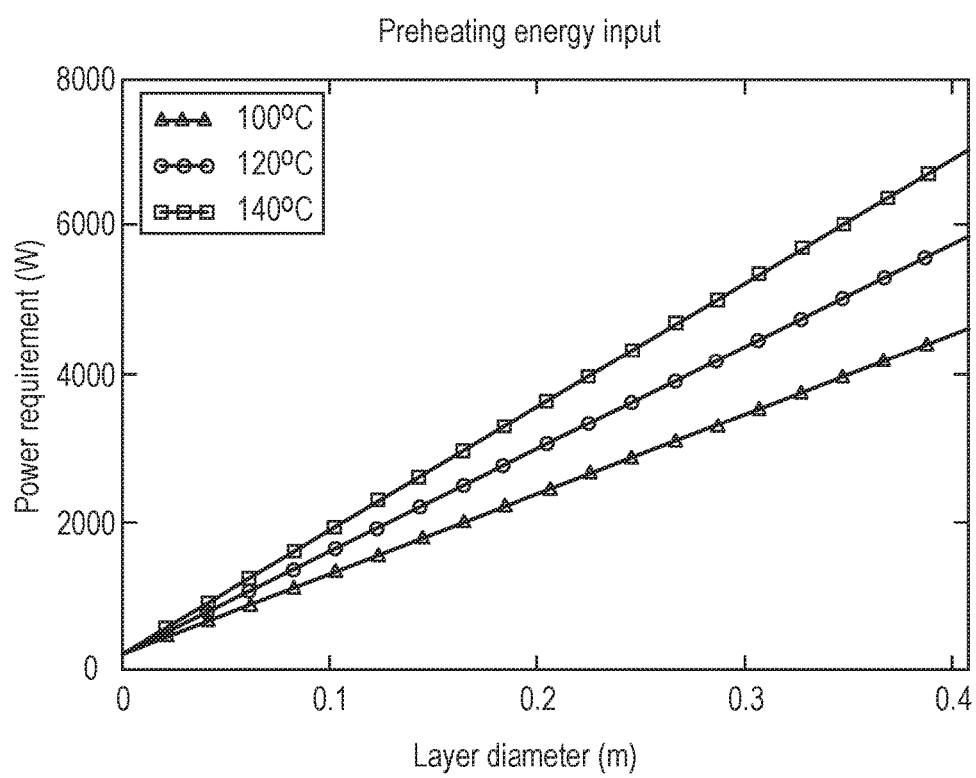
Figure 25:
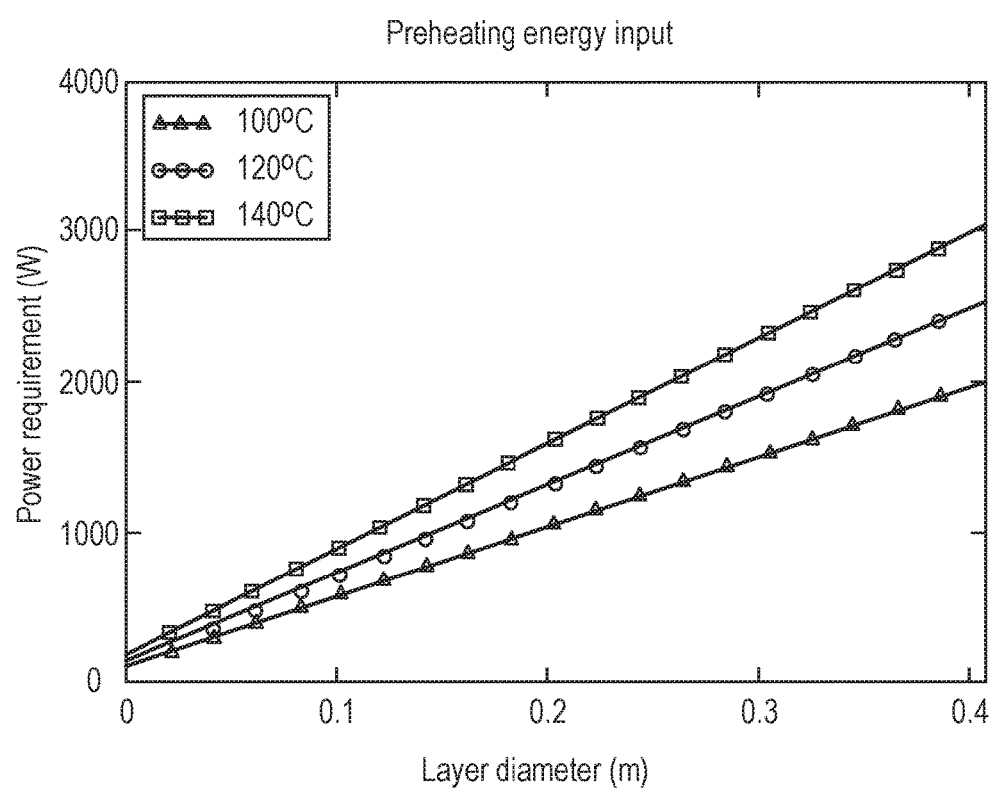
Figure 26:
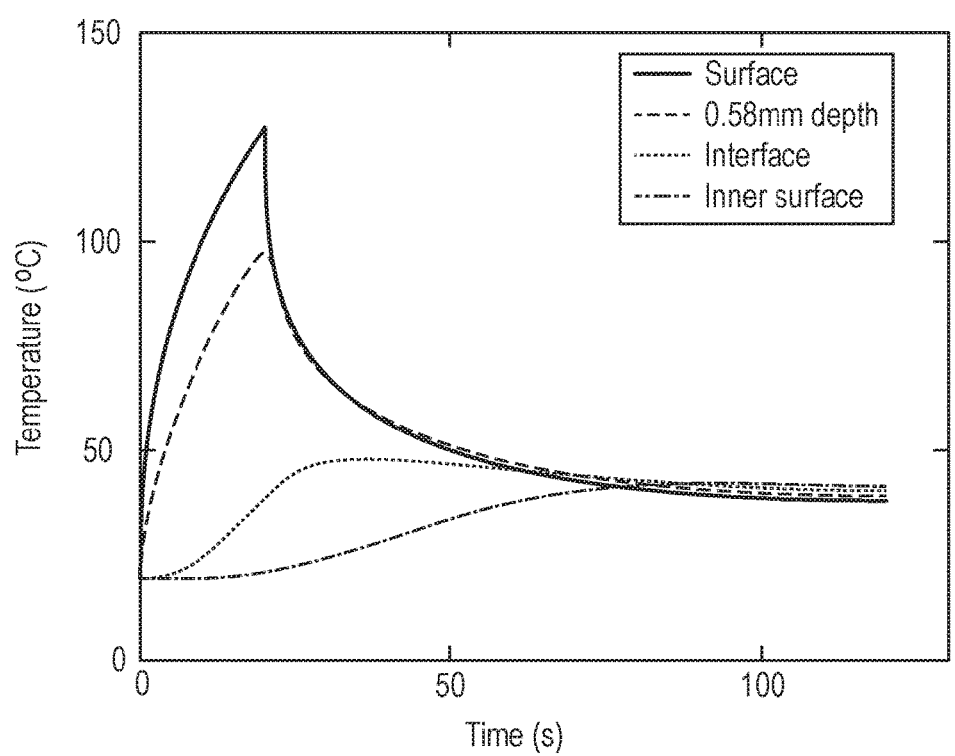
Figure 27:
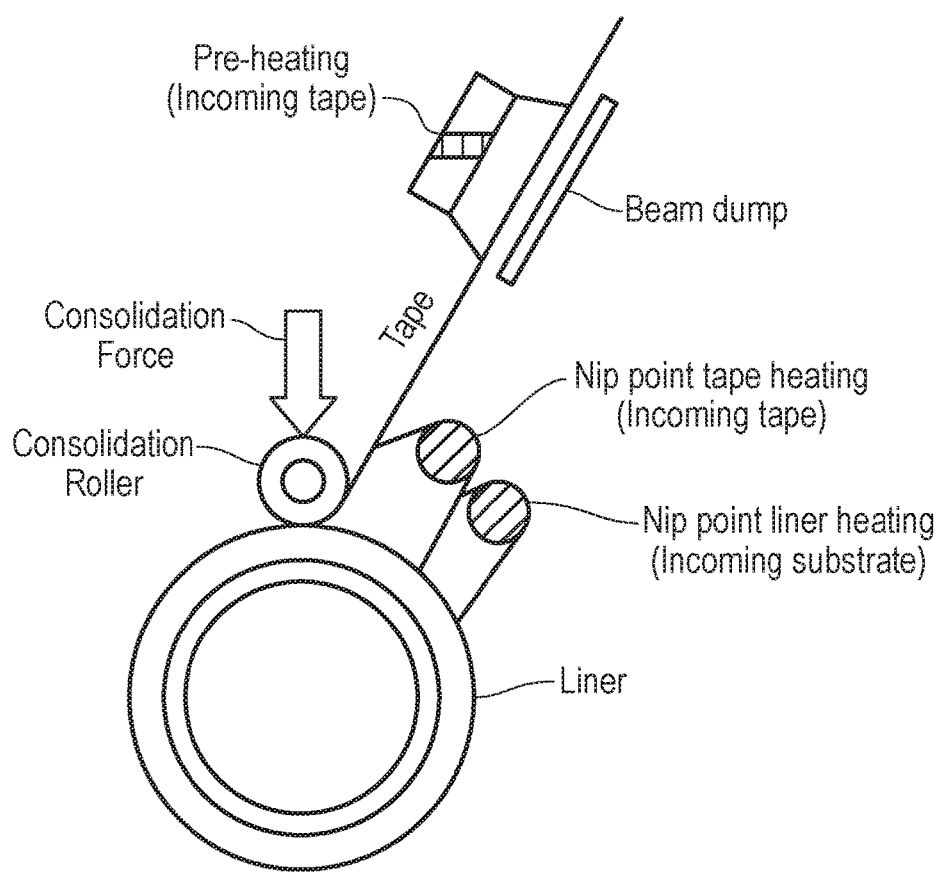
Figure 28:
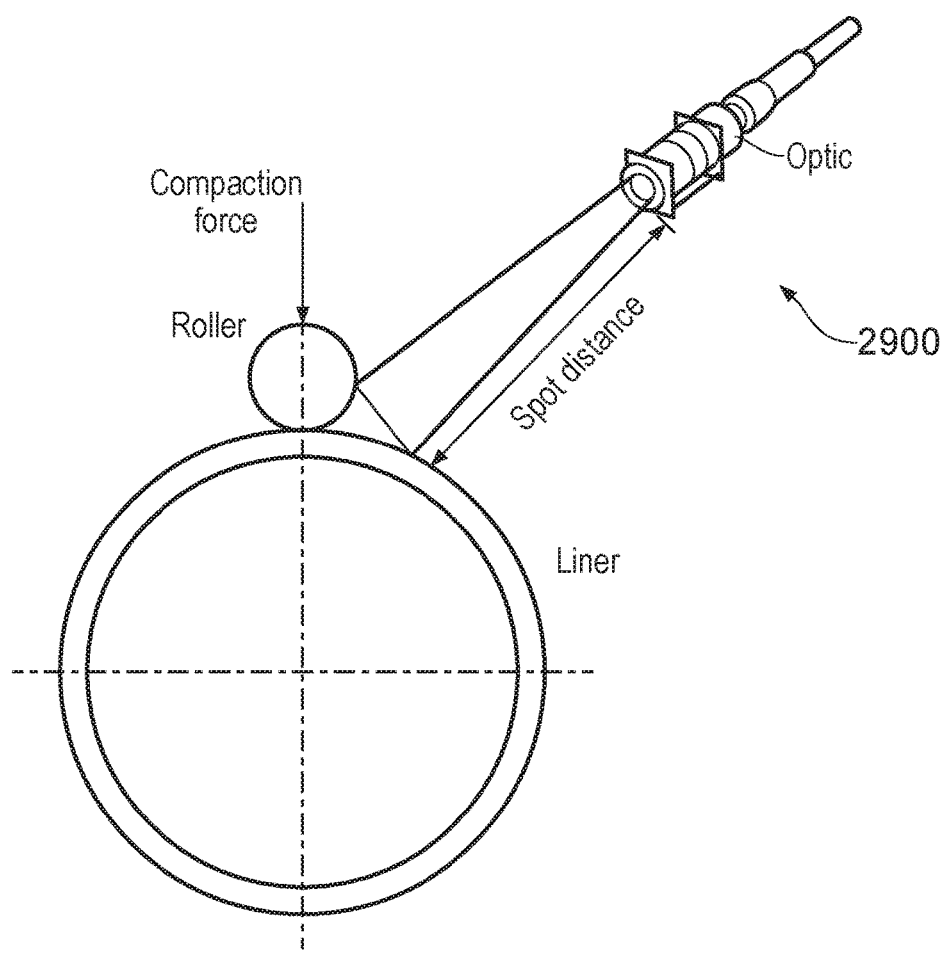
Figure 29:
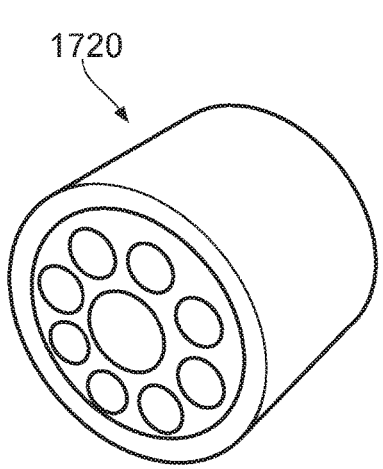
Figure 30:
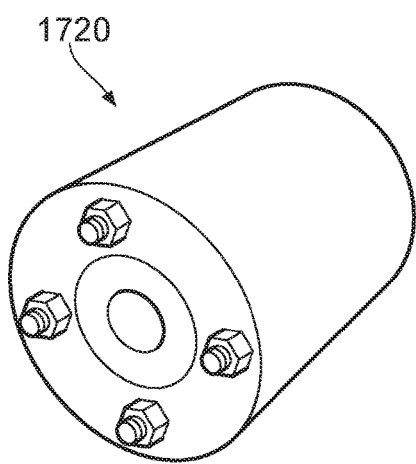
Figure 31:
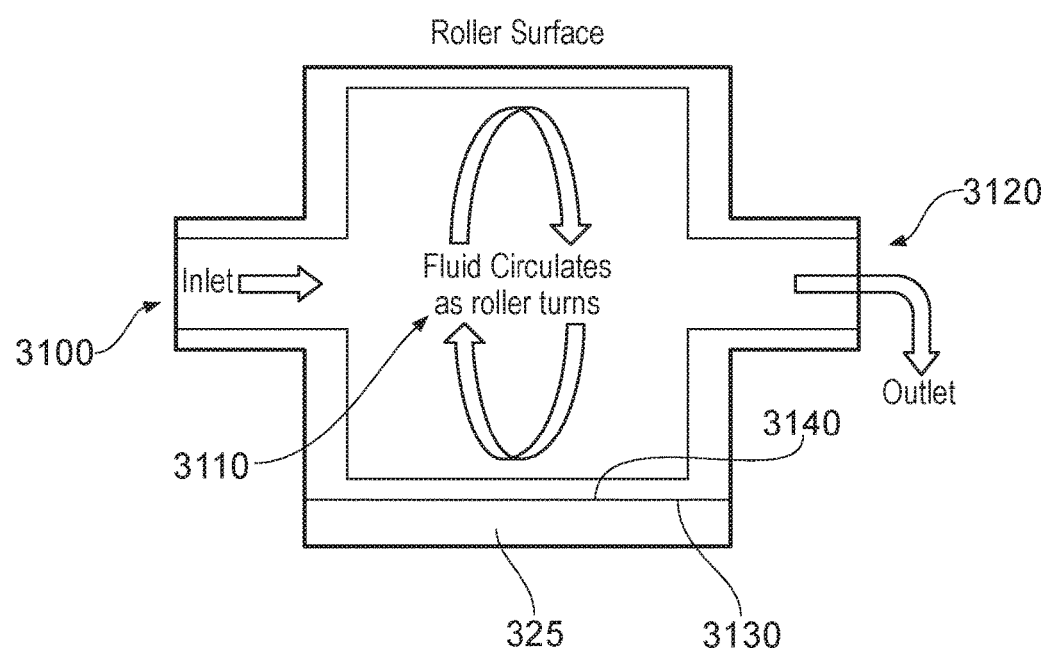
Figure 32:
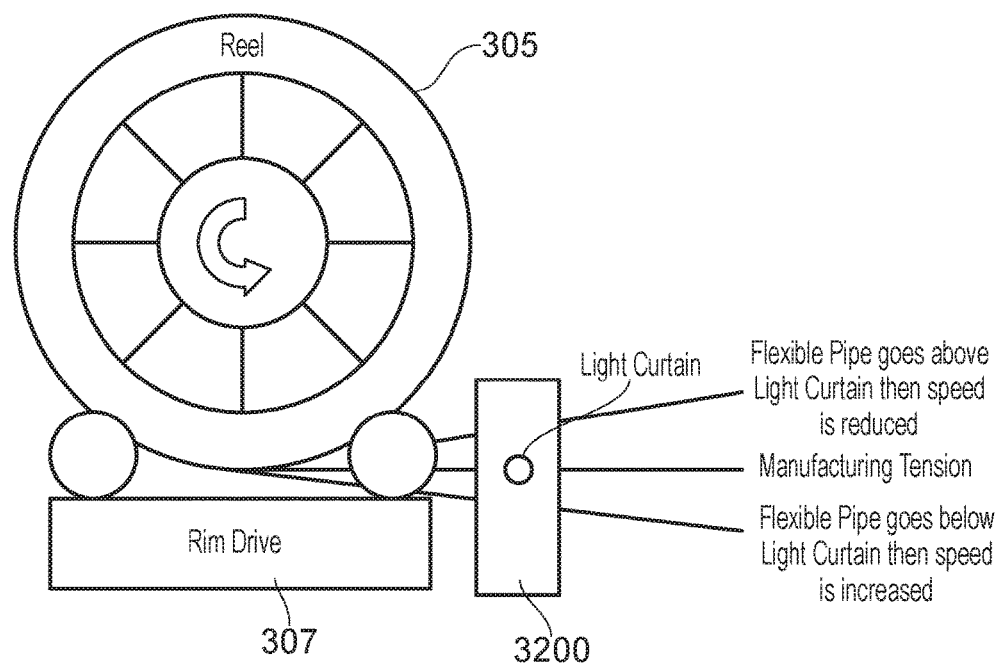
Figure 33:
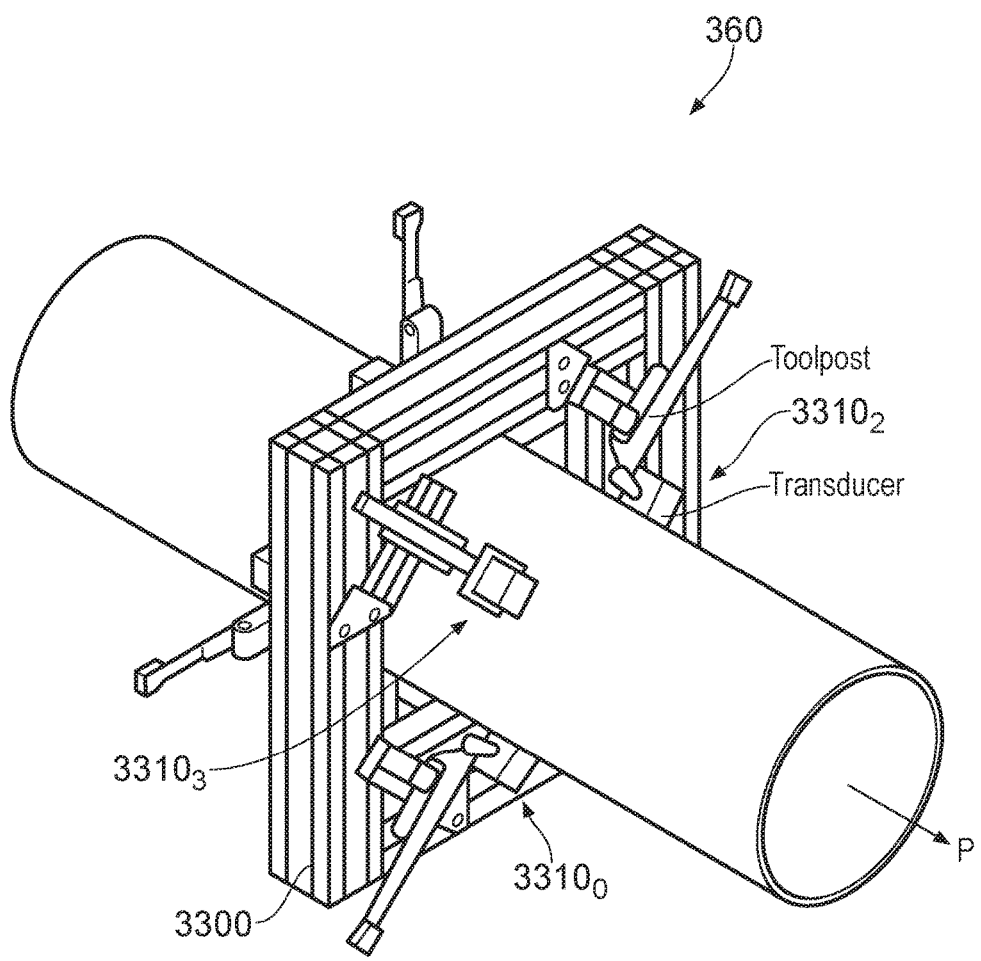
Figure 34:
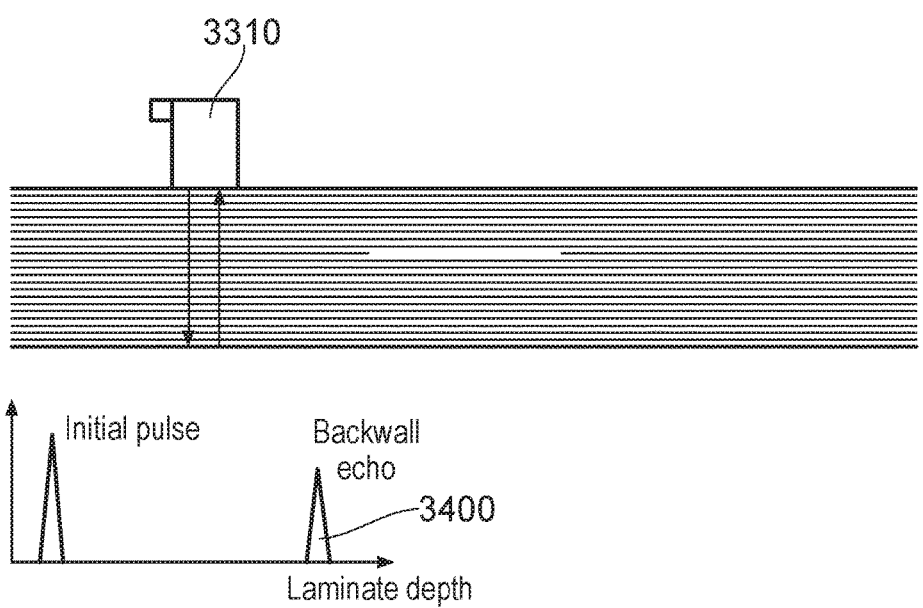
Figure 35:
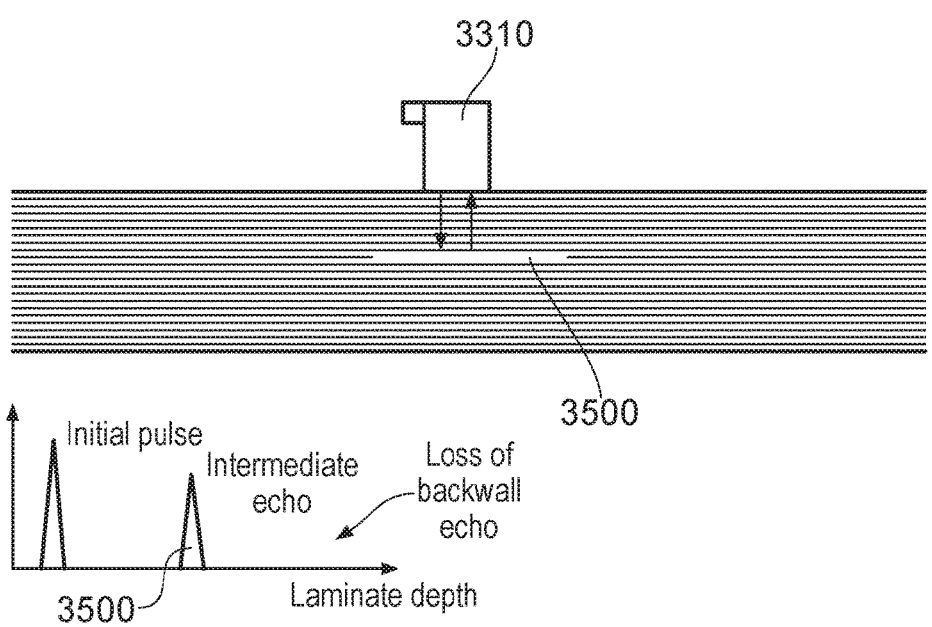
Figure 36:
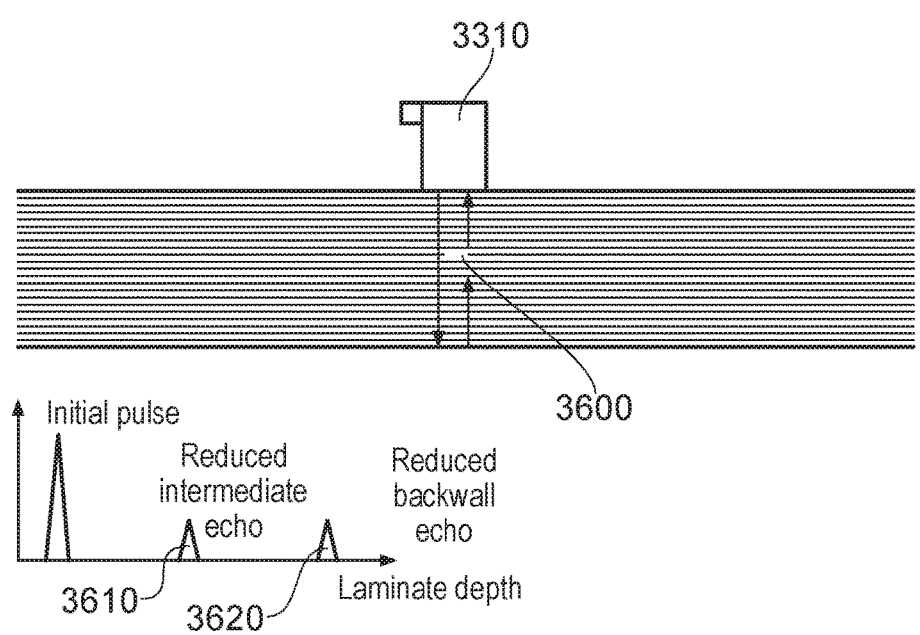
Figure 37:
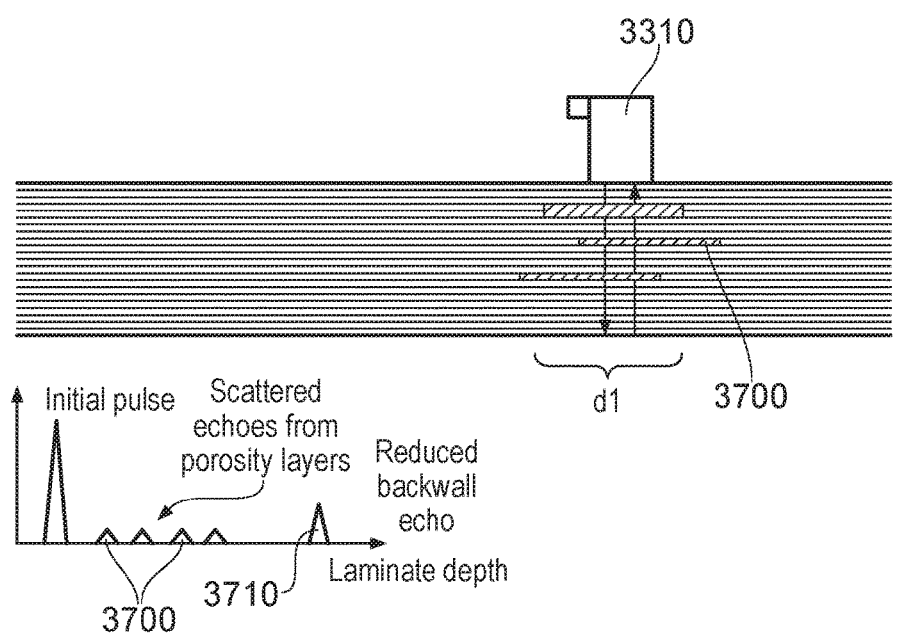
Figure 38:
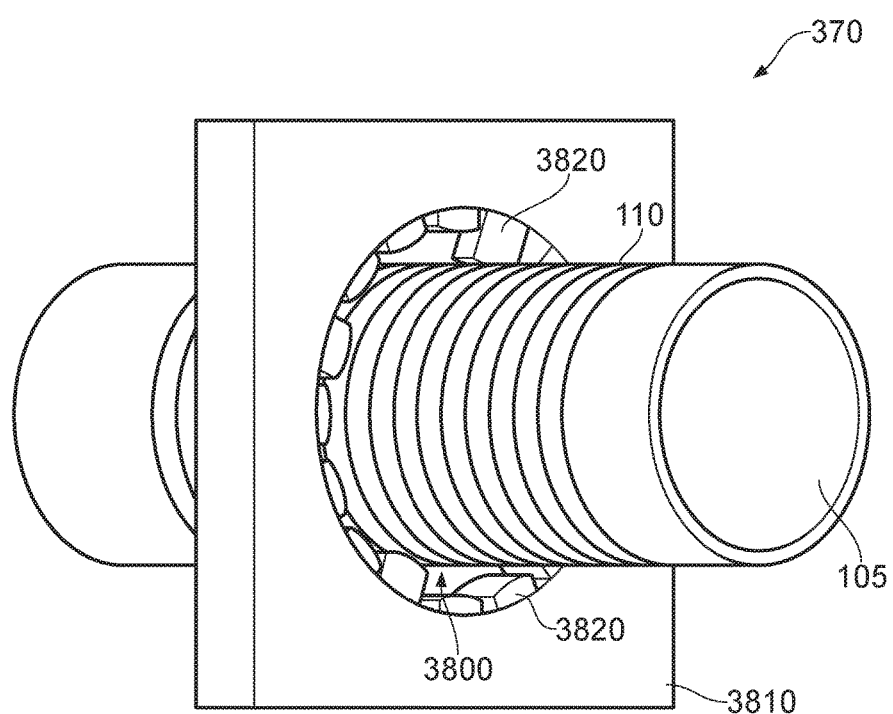
Figure 39:
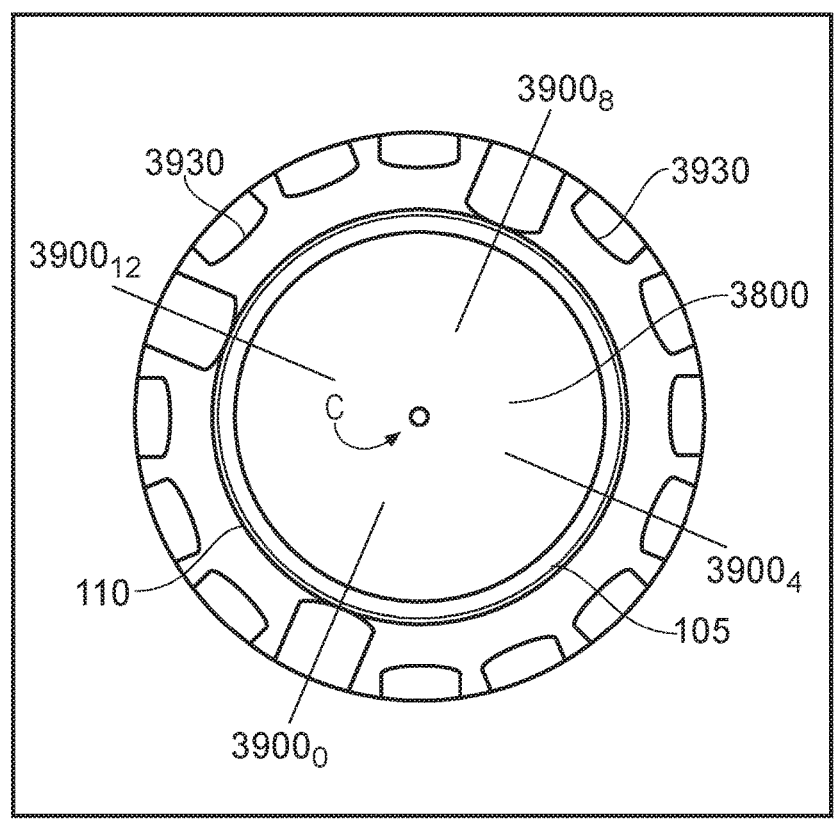

Certain embodiments of the present invention will now be described hereinafter, by way of example only, with reference to the accompanying drawings in which:

FIG. 1 illustrates bonded flexible pipe;
FIG. 2 illustrates uses of flexible pipe;
FIG. 3 illustrates a process flow map for a process of manufacturing a tubular composite layer;
FIG. 4 illustrates options for winding tape;
FIG. 5 illustrates winding tape from a supply reel to a storage spool;
FIG. 6 illustrates production of a continuous tape length;
FIG. 7 illustrates options for providing continuous tape to a tape spool for a winding carousel;
FIG. 8 illustrates a relationship with tape width and pipe diameter;
FIG. 9 illustrates rotational speed used versus pipe diameter;
FIG. 10 illustrates split spools;
FIG. 11 illustrates split spools;
FIG. 12 illustrates lifting of a spool;
FIG. 13 illustrates re-rounding;
FIG. 14 illustrates a re-rounding technique;
FIG. 15 illustrates a re-rounder;
FIG. 16 illustrates a touchdown point for tape wound over an underlying layer;
FIG. 17 illustrates consolidation of tape windings;
FIG. 18 illustrates alignment of tape with respect to a consolidation roller;
FIG. 19 illustrates guiding a pathway of tape;
FIG. 20 illustrates upstream pre-heating of a liner;
FIG. 21 illustrates pre-heating of a tape and pre-heating of a liner;
FIG. 22 illustrates power requirement for particular layer diameters;
FIG. 23 illustrates power requirement for different layer diameters;
FIG. 24 illustrates power requirement for different layer requirements;
FIG. 25 illustrates power requirement for different layer diameters;
FIG. 26 illustrates transient effects for convective heating of a pipe;
FIG. 27 illustrates pre-heating of incoming tape using infrared emitters;
FIG. 28 illustrates a laser based heating system;
FIG. 29 illustrates an alternative consolidation roller;
FIG. 30 illustrates an alternative consolidation roller;
FIG. 31 illustrates cooling of a consolidation roller;
FIG. 32 illustrates driving a reel and controlling production line tension;
FIG. 33 illustrates sensors and/or a support at an inspection station;
FIG. 34 illustrates detection of a void;
FIG. 35 illustrates detection of a void;
FIG. 36 illustrates detection of a small void;
FIG. 37 illustrates detection of one or more regions of porosity;
FIG. 38 illustrates a tubular composite layer passing through a repair station; and
FIG. 39 illustrates abutment elements at a repair station.

In the drawings like reference numerals refer to like parts.

Throughout this description, reference will be made to a flexible pipe. It is to be appreciated that certain embodiments of the present invention are applicable to use with a wide variety of flexible pipe. For example certain embodiments of the present invention can be used with respect to flexible pipe and associated end fittings of the type which is manufactured according to API 17J. Such flexible pipe is often referred to as unbonded flexible pipe. Likewise, and as described in more detail below, certain other embodiments of the present invention are usable with flexible pipe and associated end fittings for flexible pipe of a composite type structure. Such composite type flexible pipe and its manufacture is currently being standardised by the API. Such flexible pipe can include adjacent tubular layers that are bonded together.

Turning to FIG. 1 it will be understood that the illustrated flexible pipe is an assembly of a portion of pipe body and one or more end fittings in each of which a respective end of the pipe body is terminated. FIG. 1 illustrates how pipe body 100 is formed from a combination of layered materials that form a pressure-containing conduit. As noted above although a number of particular layers are illustrated in FIG. 1, it is to be understood that certain embodiments of the present invention are broadly applicable to coaxial pipe body structures including two or more layers manufactured from a variety of possible materials where at least one layer is a tubular composite layer. It is to be further noted that the layer thicknesses are shown for illustrative purposes only. As used herein, the term "composite" is used to broadly refer to a material that is formed from two or more different materials, for example a material formed from a matrix material and reinforcement fibres. Certain other possible examples are described herein below.

A tubular composite layer is thus a layer having a generally tubular shape formed of composite material. The layer may be manufactured via an extrusion, pultrusion or deposition process or, as described hereinafter, by a winding process in which adjacent windings of tape which themselves have a composite structure are consolidated together with adjacent windings. The composite material, regardless of manufacturing technique used, may optionally include a matrix or body of material having a first characteristic in which further elements having different physical characteristics are embedded. That is to say elongate fibres which are aligned to some extent or smaller fibres randomly orientated can be set into a main body or spheres or other regular or irregular shaped particles can be embedded in a matrix material, or a combination of more than one of the above. Aptly the matrix material is a thermoplastic material, aptly the thermoplastic material is polyethylene or polypropylene or nylon or PVC or PVDF or PFA or PEEK or PTFE or alloys of such materials with reinforcing fibres manufactured from one or more of glass, ceramic, basalt, carbon, carbon nanotubes, polyester, nylon, aramid, steel, nickel alloy, titanium alloy, aluminium alloy or the like or fillers manufactured from glass, ceramic, carbon, metals, buckminsterfullerenes, metal silicates, carbides, carbonates, oxides or the like.

The pipe body 100 illustrated in FIG. 1 includes an internal pressure sheath 105 which acts as a fluid retaining layer and comprises a polymer layer that ensures internal fluid integrity. The layer provides a boundary for any conveyed fluid. It is to be understood that this layer may itself comprise a number of sub-layers. It will be appreciated that when a carcass layer (not shown) is utilised the internal pressure sheath is often referred to by those skilled in the art as a barrier layer. In operation without such a carcass (so-called smooth bore operation) the internal pressure sheath may be referred to as a liner. Such a liner 105 is illustrated in FIG. 1.

It is noted that a carcass layer where it is used is a pressure resistant layer that provides an interlocked construction that can be used as the innermost layer to prevent, totally or partially, collapse of the internal pressure sheath 105 due to pipe decompression, external pressure, and tensile armour pressure and mechanical crushing loads. The carcass is a crush resistant layer. It will be appreciated that certain embodiments of the present invention are thus applicable to 'rough bore' applications (with a carcass). Aptly the carcass layer is a metallic layer. Aptly the carcass layer is formed from stainless steel, corrosion resistant nickel alloy or the like. Aptly the carcass layer is formed from a composite, polymer, or other material, or a combination of materials. Aptly the carcass layer can be substituted for a bonded reinforcement layer outside of the internal pressure sheath, which also acts as a pressure armour layer 110.

A pressure armour layer 110 is a pressure resistant layer that provides a structural layer that increases the resistance of the flexible pipe to internal and external pressure and mechanical crushing loads. The layer also structurally supports the internal pressure sheath. Aptly as illustrated in FIG. 1 the pressure armour layer is formed from a tubular composite layer. Aptly for unbonded type flexible pipe (not shown) the pressure armour layer consists of an interlocked construction of wires with a lay angle close to 90°. Aptly in this case the pressure armour layer is a metallic layer. Aptly the pressure armour layer is formed from carbon steel, aluminium alloy or the like. Aptly the pressure armour layer is formed from a pultruded composite interlocking layer. Aptly the pressure armour layer is formed from a composite formed by extrusion or pultrusion or deposition or winding of layers of tape material wherein the layers of pre-impregnated composite tape, or alternate layers of composite tapes and polymer tapes are consolidated and bonded together and also bonded to the internal pressure sheath 105 together forming a bonded pipe body structure.

The flexible pipe body also includes an optional first tensile armour layer 115 and optional second tensile armour layer 120. Each tensile armour layer is used to sustain tensile loads and optionally also internal pressure. Aptly for some flexible pipes the tensile armour windings are of metal (for example steel, stainless steel or titanium or the like). For some composite flexible pipes the tensile armour windings may be polymer composite tape windings (for example provided with either thermoplastic, for instance nylon, matrix composite or thermoset, for instance epoxy, matrix composite). For unbonded flexible pipe the tensile armour layer is typically formed from a plurality of wires. (To impart strength to the layer) that are located over an inner layer and are helically wound along the length of the pipe at a lay angle typically between about 10° to 55°. Aptly the tensile armour layers are counter-wound in pairs. Aptly the tensile armour layers are metallic layers. Aptly the tensile armour layers are formed from carbon steel, stainless steel, titanium alloy, aluminium alloy or the like. Aptly the tensile armour layers are formed from a composite, polymer, or other material, or a combination of materials.

Aptly the flexible pipe body includes optional layers of tape (not shown) which help contain underlying layers and to some extent prevent abrasion between adjacent layers. The tape layer may optionally be a polymer or composite or a combination of materials. Tape layers can be used to help prevent metal-to-metal contact to help prevent wear. Tape layers over tensile armours can also help prevent "birdcaging".

The flexible pipe body also includes optional layers of insulation 125 and an outer sheath 130, which comprises a polymer layer used to protect the pipe against penetration of seawater and other external environments, corrosion, abrasion and mechanical damage. Any thermal insulation layer helps limit heat loss through the pipe wall to the surrounding environment.

Each flexible pipe comprises at least one portion, sometimes referred to as a segment or section of pipe body 100 together with an end fitting located at at least one end of the flexible pipe. An end fitting provides a mechanical device which forms the transition between the flexible pipe body and a connector. The different pipe layers as shown, for example, in FIG. 1 are terminated in the end fitting in such a way as to transfer the load between the flexible pipe and the connector.

FIG. 2 illustrates a riser assembly 200 suitable for transporting production fluid such as oil and/or gas and/or water from a sub-sea location 221 to a floating facility 222. For example, in FIG. 2 the sub-sea location 221 includes a sub-sea flow line 225. The flexible flow line 225 comprises a flexible pipe, wholly or in part, resting on the sea floor 230 or buried below the sea floor and used in a static application. The floating facility may be provided by a platform and/or buoy or, as illustrated in FIG. 2, a ship. The riser assembly 200 is provided as a flexible riser, that is to say a flexible pipe 240 connecting the ship to the sea floor installation. The flexible pipe may be in segments of flexible pipe body with connecting end fittings.

It will be appreciated that there are different types of riser, as is well-known by those skilled in the art. Certain embodiments of the present invention may be used with any type of riser, such as a freely suspended (free, catenary riser), a riser restrained to some extent (buoys, chains), totally restrained riser or enclosed in a tube (I or J tubes). FIG. 2 also illustrates how portions of flexible pipe can be utilised as a jumper 250.

FIG. 3 illustrates a process for manufacturing a layer of a flexible pipe. The manufacturing system 300 includes a first reel 305 which is driven by a respective rim drive 307 at a respective first end of a production line. A further reel 310 is driven by a further rim drive 312 of the production line. These reels are driven selectively so as to move partially or fully constructed flexible pipe body forwards and backwards along a central axis of production 315. A direction of production is defined according to a direction in which the flexible pipe body is transported in any single pass along the production line. A respective layer can be added per pass. Alternatively additional winding, rounding, consolidation and optionally inspection modules may be utilised to provide additional layers in one production operation. In FIG. 3 a direction of production for a particular layer is shown which runs left to right. A first caterpuller unit 317 helps pull the partially or fully constructed flexible pipe body along the production axis 315 and the further caterpuller unit 320 is located at the further end of the production line to again help pull the fully or partially constructed flexible pipe body along the production line. The caterpullers can optionally be bidirectional or unidirectional. Tension in the part or fully constructed pipe body can be controlled. Aptly at least two caterpullers or tensioners are provided to grip pipe and help control line speed. These can be located as illustrated in FIG. 3 or at other locations along a production line as will be appreciated by those skilled in the art. Each of the two tensioners illustrated in FIG. 3 comprises three grip jaws (tracks) mounted at an angle of 120° to each other such that one track, the lowest, provides a horizontal surface onto which the pipe will be laid out and the other two can be respectfully retracted and returned to clamp onto the pipe. Tensioners may alternatively have two or four or more tracks if desired. The tracks are opened and closed hydraulically and are mechanically linked so that they open and close in synchronisation and that a centre line height of the pipe gripped within the tracks remain constant. If a pipe diameter decreases during running the tracks of each caterpuller can optionally follow the pipe to maintain a constant pressure on the pipe. Likewise if a pipe diameter increases the tracks are arranged to open at a pre-set pressure point. Aptly rotation of the tracks is powered in both directions electrically.

Aptly performance specifications for each caterpuller shown in FIG. 3 are set out in Table 1 illustrated below.

TABLE 1

| Specification | Notes |
| --- | --- |
| No of Tracks | 3 |
| Max pipe pull force (Te) | 6.35 (7 US tons) |
| Track Contact Length | 1778 |
| Grip Force per track (kN) | 1.4~84.0 |
| Max Product Dia (mm) | 406 (19") |
| Min Product Dia (mm) | 76 (2") |
| Centre Line Height (mm) | 1200 |
| Max Line Speed (m/min) | 5 |
| Track Shoe Angle (Deg) | 152 (angle between the two faces of each shoe in contact with the pipe. |
| Track Shoe Material | Polyurethane (Shore hardness TBC) |
| Track width | 140 mm (As per current designs) |

Certain embodiments of the present invention provide a method and apparatus for producing a bonded composite layer for a broad range of pipe diameters. This range is illustrated below in Table 2. It will be appreciated that other pipe diameters can be made.

TABLE 2

| Pipe I/D Range (Inches) | Approx. finished pipe O/D (Inches) | Approximate weight finished pipe (Kg/m) |
| --- | --- | --- |
| 3-4 | 5-6 | 75-125 |
| 4-6 | 6-8 | 100-200 |
| 6-8 | 8-10 | |
| 8-12 | 10-12 | |
| 10-12 | 12-14 | |
| 12-14 | 14-16 | 150-250 |
| 14-16 | 16-18 | |

The manufacturing system 300 illustrated in FIG. 3 uses a winding station 322 such as a winding carousel to wind composite tape 325 onto a cylindrical surface formed by an underlying layer. Tape is provided to the winding carousel 322 from multiple spools $327_{0-3}$. Each tape spool 327 is provided with a respective feed supply of a continuous tape 328. Aptly manufacturing a bonded composite layer makes use of a continuous tape feed 328. To achieve this, shorter lengths of composite tape are spliced together prior to being wound onto a tape storage spool. An optional re-winder 330 is utilised to help carry out this operation. Raw material 332 in the form of premade tape of fixed length is supplied in relatively short lengths and spliced together before storing on a storage spool 333. In use a rewind/unwind unit 335 is used to wind these longer lengths of tape onto respective tape spools $327_{0-3}$ for use at the winding carousel 322. Aptly the winding station comprises an accumulator unit (not shown) which allows successive tape spools/tape lengths to be joined without arresting the production process.

In the system 300 illustrated in FIG. 3 a re-rounder station 340 is utilised to control the tolerance in terms of ovality of an incoming underlying layer of flexible pipe body. That is to say the re-rounder can help round a cross section of an underlying layer so that a cylindrical outer surface provided by the underlying layer is substantially round. Aptly the re-rounder may be positioned anywhere before the tape winding provided that the incoming layer remains re-rounded until after the tape is applied. Aptly the underlying layer is a liner and the winding carousel provides tape that helps form an overlying pressure armour layer as a tubular composite layer. The re-rounder station 340 is optional. Aptly an additional re-rounder station (not shown) is provided downstream of a consolidation station 350.

As illustrated in FIG. 3 a tape consolidation station 350 is provided downstream of the winding station 322. That is to say the consolidation station, which is an arrangement of associated equipment and control elements is located further along in a direction of transportation of the flexible pipe body as a particular layer is manufactured. The consolidation station 350 helps consolidate adjacent windings $325_a$, $325_b$ of composite tape so that adjacent windings are consolidated together to form a tubular composite layer. It is to be noted that optionally the consolidation unit may alternatively or additionally consolidate a layer in the sense of consolidating tape in a most recently applied layer with the material of an underlying layer about which the tape is wound. Multiple winding and consolidation units may be included in series to help build up additional thickness of the tubular composite layer if desired.

As illustrated in FIG. 3 the manufacturing system 300 also includes a non-destructive testing (NDT) inspection station 360. This is located downstream of the winding carousel 322 and consolidation station 350. The inspection station 360 includes one or more sensors and is arranged in an in-line configuration with the winding station 322 shown in FIG. 3. The winding station 322 and consolidation unit 350 provide a tubular composite layer and the inspection station 360 automatically and continuously determines if at least one parameter of the tubular composite layer satisfies a respective predetermined condition in one or more regions of the tubular composite layer as the tubular composite layer is transported through or near to the inspection station. The inspection station also provides a real time output which indicates at least one of a type, size and/or location or other such characteristic of any defect in the tubular composite layer as it is made. Aptly the inspection station senses if parameters are different from an expected 'ideal' and determines if a defect is present and what type that defect is. Multiple NDT stations may optionally be included in the production line to help and inspect each respective composite layer after it has been applied, or to help inspect repairs carried out at a post process repair station 370 (as described further herein after).

A post-process repair station 370 is shown in FIG. 3 downstream of the inspection station 360. The repair station 370 receives input control responsive to the output from the inspection station and includes heating and/or pressure and/or cooling elements which can be brought to bear on the regions of the tubular composite layer where a defect has been identified. As such the repair station 370 can entirely or at least partially help to correct the defects in real time and in an in-line single production process. This helps avoid the need for after the event analysis and subsequent remedial action.

As illustrated in FIG. 3 a user interface 370 which includes a user display at an analysis and control station 380 can be utilised to control the parameters of the overall manufacturing system 300. For example line speed and/or winding speed and/or consolidation temperatures and pressures and/or inspection techniques and/or re-rounding action and/or post process defect repair can be selectively controlled.

Manufacture of a continuous bonded composite layer for a flexible pipe requires a predetermined amount of raw material. Significant lengths of raw material in the form of tape for winding at a winding station can be used. Aptly the length of continuous tape wound in a winding station 322 is 500 m or more in length. As a result of this a re-wind operation can be utilised within a pipe manufacturing facility which makes use of the manufacturing system 300 illustrated in FIG. 3. Aptly the length of each tape used in a re-winding station 330 is about around 100 to 300 m. Aptly the length of each tape used in a re-winding station is about around 250 m. The re-winding process is optionally configured to supply tape directly into tape spools $327_{0-3}$. FIG. 4 helps illustrate the re-winding process in which raw material from a manufacturer is provided from a spool 400 in the form of composite tape of a fixed relatively short length. Manufacturing a bonded composite layer requires a longer continuous tape feed. To help achieve this, lengths of composite tape provided as raw material on a spool 400 are spliced together at a splicing station 410 prior to being wound. Winding occurs either directly into the winding station/winding carousel 420 (illustrated as task 1) or optionally onto a tape storage spool in an off-line re-wind station (illustrated as task 2). It should be noted that tape may also be wound out of the winding station (illustrated as task 3) onto an external tape storage spool in order to remove left-over material at the end of any production run or in order to change materials/material properties of the tapes part way through a production run.

FIG. 5 helps illustrate the process of splicing shorter raw material lengths of composite tape together to form longer continuous tape lengths on a tape spool 420. It may be noted that the receiving tape spool(s) may be on the production line $327_{0-3}$ or off-line to be substantially fed onto the on-line spool(s). A supply wheel 400 of raw material is driven by/pulled from an adjustable brake/tension pay-off unit 500.

This tape which is incoming from the supply reel 400 is guided by a guided roller 510 through a first clamp element 520 and is then fed between a joining press 530. The joining press splices opposed ends of a preceding length of tape to a leading end of a new tape length. A further clamp 540 helps secure a trailing end of a preceding tape in position to be joined with the leading end of the new tape length. A further guide roller 540 is used to help guide the tape to the storage spool 420 which is driven by a drive and brake unit 560.

FIG. 6 helps illustrate the joining press 530 shown in FIG. 5 in more detail. The joining press 530 includes an upper heated plate 610 and opposed lower heated plate 620. A leading end 630 of a new incoming length of composite tape is located juxtaposed with a trailing end 640 of a previously provided length of tape. By urging the two opposed heated plates together at a desired temperature two shorter lengths of tape can be extended in length. By repeatedly carrying out this process multiple shorter lengths of tape can be secured together to effectively provide a continuous tape feed. This process can be automated by using sensors not shown to identify and align tape ends. Optionally, of course, suitable large lengths of needed tape can be supplied in which situation the joining of shorter lengths is not necessary.

Aptly in order to help minimise a movement of raw material to and from a tape winding carousel the re-winding operation is located proximate to the winding station. The re-winding unit is also capable of servicing multiple tape modules. This is illustrated in FIG. 7 which illustrates how a tape storage zone 700 can be used to store incoming supply reels from manufacturers and how these can be loaded in an automated or at least semi-automated way onto a re-winder positioned at a desired location shown as a first and second location $710_0$, $710_1$ which can then be used to refill a respective storage spool 420 (either off-line or in-line) for a specific composite tape prior to provide a continuous tape to a particular tape spool that feeds the winding station. The storage spool and/or re-winder unit move selectively along respective rails 720, 730 to align re-winders and storage spools and/or tape spools $327_{0-3}$ supply the winding carousel 322.

Aptly the storage zone can house both empty and loaded tape spools. Aptly the facility is able to store multiple different sizes of spools. Aptly the storage zone is a region close to the winding station that provides access to a spool via an overhead crane.

Manufacturing of a bonded composite layer requires a tape of predetermined width, thickness and length. Aptly multiple spools, each designed and manufactured for use with a specific tape width and storage capacity are provided. Tape storage spools can be provided for tape widths of 10 mm, 20 mm, 60 mm and/or 80 mm or the like.

FIG. 8 illustrates a relationship with tape width and nominal pipe diameter for a total tape width which produces a single cover in one path for target angles of 80°, 83° and 85°. A nominally 8" pipe at 83° requires a tape width of 80 mm for a single cover. Aptly this is split into two strands at 40 mm or four strands at 20 mm to achieve the same cover but with corresponding numbers of tape heads.

FIG. 9 helps illustrate a rotational speed used to produce a single cover at 1 m/min linear speed versus pipe diameter. Speed remains constant if a single tape is used or the tape is split into two or four. The difference is that of heat input which can optionally be applied through several tape heads.

Using the re-winder, raw material is wound onto the tape storage spools offline prior to commencing production. The spools are capable of accommodating a number of tape widths as previously mentioned. In addition, spools are optionally designed so that they can be split into two halves. This is illustrated in FIGS. 10 and 11 in more detail. As illustrated a splittable spool 1200 includes a first portion 1210 illustrated as a top portion in FIG. 10 and a further portion 1220 illustrated as a bottom portion in FIG. 10. Should the occasion/need arise, this allows for spools to be unwound and removed or loaded and rewound in use whilst a pipe is running through a centre of the carousel. The split spools 1200 illustrated in FIGS. 10 and 11 can thus be utilised as the tape spools $327_{0-3}$ illustrated in FIG. 3. Aptly a multi-part can be separated into more than two parts. Aptly the spool is provided with lifting points to allow loading or unloading of either a full spool or half section using an overhead crane. FIG. 12 helps illustrate how optionally a rim 1300 of a spool can be formed so as to form a channel 1310. The channel which can be continuous around a whole circumference of a spool or optionally is only located in particular locations can be engaged by a mating lifting hook 1320 of a lifting crane and used as a lifting point. Other lifting mechanisms could of course be used on a spool.

To help improve a tape laying process and ensure good concentricity of the pipe prior to tape laying, a method of re-rounding the existing layer or layers of flexible pipe body can optionally be utilised. Aptly a re-rounding station 340 can be utilised immediately before a tape consolidation step. FIG. 13 helps illustrate how a re-rounder can be utilised to provide a variable pressing force (illustrated by arrows F) at selected locations around a circumference of a cross section of a tubular layer such as a liner or a liner and overlying tubular composite layer or the like. Aptly a re-rounder is utilised for pipe structure re-rounding when no carcass is present. Aptly the re-rounder is able to re-round a tubular layer having an outer diameter of between 2" and 19". Aptly the re-rounder is able to re-round tubular layers having an outer diameter of between 6" and 16". The re-rounder is capable of exerting a force or pressure uniformly on the outer circumference to achieve a pre-set ovality tolerance.

FIG. 14 helps illustrate the action of a re-rounder 1500 at a re-rounder station 340. It will be appreciated that a re-rounder station includes the re-rounder together with ancillary equipment and control equipment to control operation of the re-rounder. As illustrated in FIG. 14 the re-rounder can be provided by a compressive dye 1510 that can be provided circumferentially around an outer surface of a tubular layer at a fixed position with respect to a direction of production. Aptly the dye material is of low friction (for instance PTFE or the like) and the contact surface is smooth so that the progress of the tubular layer is not adversely inhibited, nor damaged by the re-rounding process.

FIG. 15 illustrates an alternative re-rounder 1600 which includes six rollers 1610$_{0-5}$ which have a generally figure of eight shaped outer running surface which has a concave shape with an arc corresponding to the shape of an outer surface of the flexible pipe layer being rounded. In FIG. 15 the tubular layer/pipe being re-rounded runs in and out of the page. The circumferential position of rolls may be rotatably positioned and aligned with ovality based on measurements from a previous inspection station. Each roller rolls along a respective longitudinal axis and is supported by a roller support 1620$_{0-5}$ which is spring loaded via a respective spring 1630$_{0-5}$. The spring is a biasing element that biases a respective roller constantly against the outer surface of the tubular layer. Alternatively the rollers can be hydraulically driven or pneumatically driven or are otherwise actuated. Sets of rollers suitable for certain pipe size ranges may optionally be configured into the same re-rounder tool so that they can be rotated or otherwise moved in and out of position to act on a respective size of pipe in use at that moment in time. A result of this set up is to reduce the time required to change from one pipe diameter to another.

FIG. 16 helps illustrate the touchdown point by the winding carousel of the winding station 322 in more detail. The touchdown point 1700 is the location on a cylindrical outer surface of an underlying substantially tubular element at which incoming continuous lengths of tape touch the outer surface of the underlying cylindrical surface. For example, as illustrated in FIG. 16 an incoming tape 325 is wound off a respective tape spool 327 and is transported in a direction illustrated by the arrow A. The tape 325 is duly located between a pair of opposed rollers 1710 which nip the tape. One or more of the rollers is driven so as to provide a desired tape tension. One or more heaters (not shown) can be located upstream and/or downstream of a pair of opposed rollers 1710 to pre-heat the incoming tape to a desired temperature. The tape is then fed along a tape supply pathway to a point between a cylindrical outer surface provided by a liner and an opposed consolidation roller 1720. A consolidation force is supplied to the consolidation roller by a biasing element which in the example described is a spring or may optionally alternatively be a hydraulic or pneumatic actuator (not shown). This consolidation force is continuously controlled and monitored via the control station 380.

As illustrated in FIG. 16 a longitudinal axis associated with the roller is substantially aligned in a parallel offset fashion with a longitudinal axis associated with the liner 105. One or more heaters and/or coolers (not shown) are arranged around the liner so as to pre-heat the liner material to a predetermined temperature prior to the touchdown of tape. One or more heaters and/or coolers are also located so as to be able to control the nip point temperature. That is to say a temperature at the point where tape touches down onto the outer surface of the liner. The continuous length of tape 325 is thus unwound from a storage spool and directed along a set path to the touchdown point on the pipe. To achieve good tape consolidation various parameters can be controlled along the route. These parameters include but are not limited to tape tension, tape angle, tape pre-heat temperature, tape gap, heated consolidation temperature, liner pre-heat temperature and consolidation force. Aptly tape tension is varied from 10N to 200N. Aptly a default tolerance on the set tape tension is plus or minus 3N. Aptly a wrap angle of between about around 55° to 90° is utilised. A live adjustable closed loop system with feedback to control and monitor tape tension can optionally be included. Aptly a consolidation force is varied from about around 5N to 400N with a default tolerance on any predetermined pre-set value of plus or minus 3N. A live adjustable closed loop system with feedback to control and monitor consolidation force can optionally be utilised. A tape wrap angle of between about around 55° to 90° can be used. Individual tooling can optionally be provided in 5° increments to allow manufacturing of tape angles across this range. Aptly each set of tooling can be provided to allow fine adjustments of plus or minus 3°.

FIG. 17 helps illustrate how a gap between adjacent tape windings can be controlled as the tape is wound. It will be understood that the underlying cylindrical surface, provided by an outer surface of the liner in the example shown in FIG. 17, is continually moving in a production direction illustrated by the arrow P in FIG. 17. Aptly the line speed in the production direction is about around 0.25 to 2 m/min. Aptly the line speed is about around 1 m/min. As the underlying layer advances, new tape winding, which is constantly wound helically around the cylindrical surface of the underlying layer by the rotating winding carousel, likewise advances so that on a next pass around the underlying layer a newly incoming winding abuts in a side-by-side arrangement with an immediately preceding winding. Aptly no overlap occurs between adjacent windings. Aptly adjacent edges of adjacent side-by-side windings abut. Aptly a gap 1800 of about around 0-50% of the tape width is left between tape windings 1810$_{0-4}$ during the wrapping process. Aptly a gap 1800 of about around 0-1 mm of the tape width is left between tape windings 1810$_{0-4}$ during the wrapping process.

To help protect the incoming tape and ensure good consolidation is achieved the path from the spool to the touchdown point on the pipe illustrated in FIG. 16 is kept within predetermined tolerances. Changes in direction along the tape path are likewise kept within predetermined tolerances. Where a change in direction takes place the change is made gradually so as to not damage the tape. Aptly the pathway followed by the incoming tape is constantly monitored and controlled to help keep the tape travelling along a centre line of the nip rollers 1710 and/or the consolidation roller 1720. FIG. 18 helps illustrate an underside view of the consolidation roller 1720 which rolls along a respective axis R. FIG. 18 helps illustrate a tape axis T and helps illustrate how this tape axis T is kept aligned with a generally central position of the consolidation roller 1720.

FIG. 19 helps illustrate how, in order to help maintain the incoming tape 325 on a predetermined pathway, one or more supply rollers such as the opposed rollers 1710 illustrated in FIG. 16 can be provided with a guide groove 2000. This guide groove is provided at a desired location on an outer running surface 2010 of one or more rollers at a predetermined location. Aptly, as illustrated in FIG. 19, the groove is located circumferentially around a centre region of a supply roller. As a result incoming tape 325 nests wholly (or at least partially in other examples) in the groove and is thereby located by the groove to keep the tape on a predetermined path as it advances towards the winding carousel.

Aptly a tape break alarm can be provided to alert machine operators that a break has occurred in a tape supply. The alarm can optionally be installed along each tape path between a respective spool and a respected touchdown point on the pipe line. The tape break alarm is aptly linked to a closed loop system monitored by the control station 380 so that action can be promptly taken to stop a manufacturing process and initiate remedial action if a tape break event occurs. Aptly a monitor for monitoring the amount of material being unwound from any spool or by the winding carousel can be provided. Information from such a monitor is used to generate a display on the display of the control station so that an operator can constantly watch one or more parameters of production. Aptly an amount of material unwound is converted and displayed as a measurement of linear meters of pipe made on the user interface.

As previously described the liner and/or tape can be pre-heated or immediately post heated to help during a consolidation process. FIG. 20 helps illustrate this process in more detail. Pre-heating helps reduce the operating requirements of the heating technology immediately prior to/during consolidation, (hence the power required by the consolidation heating system and/or total heat energy (and time) required to raise and maintain the temperature of the composite material during/to allow consolidation to be effective, is reduced). Aptly pre-heating is carried out as close to a tape consolidation area as possible. Aptly the liner is pre-heated to between about around 50° C. to 100° C. Aptly the liner is pre-heated to between about around 40° C. to 90° C. Aptly the tape is heated to about around 30 to 160° C. Aptly the tape is heated to about around 100 to 140° C. As illustrated in FIG. 20 as the liner 105 advances in the direction of production P and the consolidation roller 1720 urges incoming composite tape 325 onto the outer surface of the liner the incoming liner upstream of the touchdown point can be pre-heated by a heating element. As illustrated in FIG. 20 an induction heating coil 2100 can be used which is located surrounding the incoming liner. This can be used to continuously pre-heat the liner as it is transported along in the production direction P towards the supply point where composite tape is supplied onto the outer surface of the liner and urged against the outer surface by the constantly biased consolidation roller 1720.

FIG. 21 helps illustrate pre-heating of tape prior to the touchdown point and heating of a liner using infrared techniques in more detail. As illustrated in FIG. 21 a pre-heating unit 2200 is an example of a heating element which can be used between the nip rollers and the touch-down point 1700. This pre-heating unit can include a single heating element or multiple heating elements to pre-heat incoming tape to a desired temperature. Likewise liner pre-heating can be provided in the form of two (other numbers are of course possible) infrared heaters $2210_0$, $2200_1$ which are directed to desired locations to heat a liner. The heaters move in a circular direction with the rotating winding carousel so as to heat the liner before the consolidation roller, which is constantly revolving as part of the winding carousel around the outer circumference of the liner, to a desired temperature.

To help consolidate thermoplastic composite tape one or both of the tape and the substrate are heated to a melting point of the thermoplastic material used. Aptly for the tape which is a composite material, the tape if heated to the melting point of the thermoplastic matrix material of the tape. Aptly to help achieve this and bearing in mind that there is a linear line speed of about around 1 m/min likely for the underlying liner, a pre-heating step is utilised prior to tape application. This helps reduce a requirement for energy input at a tape head region.

Aptly the incoming tape is a composite material comprising a carbon fibre reinforced PVDF tape. Pre-heating requirements for tapes having a 0.2 mm and 0.4 mm thickness for such tape is illustrated in FIG. 22 and FIG. 23. As the tapes are relatively thin these figures illustrate heating from both sides of a tape to an even temperature. FIGS. 22 and 23 are based upon a pipe line speed of 1 m/min and provide an indication of energy required to heat a full thickness of tape. Aptly this is a minimum power provided. Aptly two or three times this power is provided according to a type of heater utilised. FIGS. 22 and 23 illustrate energy input for a single tape producing a complete cover. FIG. 22 illustrates a power requirement to heat a 0.2 mm thick tape to 100° C., 120° C. or 140° C. versus pipe layer diameter. FIG. 23 illustrates a power requirement to pre-heat a 0.4 mm thick tape to 100° C., 120° C. or 140° C. versus pipe layer diameter.

The substrate upon which the tape is wound is optionally pre-heated. In the instance in which the substrate is a liner which is relatively thick this presents a larger thermal mass than the incoming tape. Aptly this is heated from an outside region. Aptly heating occurs from the surface and through into the thickness of the liner to a predetermined depth. Aptly the heating depth is between about around 0 and 2 mm in depth. Aptly the heating thickness is about around 1 mm in depth. Heat input is controlled to help minimise residual stresses in a resulting structure.

FIG. 24 helps illustrate an order of magnitude calculation of a power requirement to pre-heat a PVDF liner assuming only a first outer 1 mm of thickness is heated to a uniform temperature. Energy requirement is shown to heat a whole outer surface of a liner moving at a line speed of 1 m/min. FIG. 24 thus helps illustrate power requirement to pre-heat an 8 mm PVDF liner to 100° C., 120° C. or 140° C. versus pipe outer diameter.

Pre-heating of consolidated tape requires less power as illustrated in FIG. 25. This illustrates pre-heating energy input under similar assumptions to the liner noted above but for an 8 mm thick liner with 6 mm of consolidated tape on the outside.

FIG. 26 helps illustrate transient effects for convective heating of a pipe arrangement having an 8 mm liner and 6 mm composite tape at 200 mm nominal diameter. The transients are also illustrated for the condition in which a pipe is moving at 1 m/min and this passes through a heater which raises surface temperature to 126° C. within 30 seconds, approximately 0.5 mm below the surface the temperature is 100° C. and as time progresses the heat dissipates within the structure.

Pre-heating thermoplastic composite tape utilises a relatively low power of about around 0.5 kW whilst a liner of consolidated composite pipe surface requires a power arranged around the pipe of about around 3 to 4 kW over the above-mentioned range of pipe sizes. Aptly an infrared heating system can be utilised for composite tape consolidation. Infrared emitters provide adequate consolidation whilst being relatively cost effective and simple to utilise. Aptly as an alternative a laser heating system or the like can be utilised. FIG. 27 helps illustrate pre-heating of incoming tape by infrared emitters. Use of such infrared emitters as a heating source helps reduce a requirement for installation space for additional emitters at a nip point area.

FIG. 28 illustrates a heater element in the form of a laser system 2900. Such a system can provide a good consolidation for a bonded composite layer. Aptly a compact laser diode module device is used as the laser heating element 2900. Aptly the laser heating system includes a cooling supply for a laser source and associated optics. Aptly the laser heater element is water cooled having a water pressure which does not exceed 6 bar and having a water flow of about around 10l/hr. An air purge can optionally be applied to help avoid dust contamination in a pathway of the heating laser beam. Since the laser can provide significant heating capacity the consolidation roller may optionally include cooling to help prevent the roller from overheating.

A cross section of process requirements for different tape widths and materials is illustrated below in Table 3.

TABLE 3

| Tape Width and Material | Output Power (Watts) |
|---|---|
| 1 mm width of PA12/PVDF Tape | 240-308 |
| 20 mm width of PA12/PVDF Tape | 4.800-6.160 |
| 80 mm width of PA12/PVDF Tape | 19.200-24.640 |

Table 3 helps illustrate pre-heating and nip point power required for achieving process temperature.

FIGS. 29 and 30 illustrate views of a consolidation roller. The consolidation roller 1720 presses heated tape onto an underlying layer and helps consolidate adjacent windings together and/or ensures a good bond is achieved between each successive layer of tape windings. Aptly the roller is a light weight roller manufactured from a material with low heat capacity and high thermal conductivity. Aptly the roller is covered in a non-stick material. Aptly the non-stick material is rubber based. Aptly rollers covered in approximately 10 mm thick layers of silicone or viton with a shore hardness of about 60 are used. Aptly the rollers are PTFE coated rollers with a coating thickness of approximately 40 microns plus or minus 10 microns. Aptly a solid PTFE bar can be used as a roller. FIG. 29 illustrates a silicon based roller and FIG. 30 illustrates an alternative solid PTFE consolidation roller.

FIG. 31 helps illustrate how a surface temperature of the roller can be maintained or "chilled" to below about around 120° C. This helps ensure tape fibres or resin does not adhere to a rolling surface of the roller. It will be appreciated that other ways of ensuring non-adherence can be utilised. As illustrated in FIG. 31 an inlet port 3100 is utilised to receive a supply of cooling fluid which then circulates in a central region 3110 inside the body of the roller. A further outlet port 3120 is provided at a remaining end of the roller and coolant fluid exits through this outlet port 3120. Coolant fluid is constantly circulated or alternatively provided in a one way direction. FIG. 31 also helps illustrate how a lower rolling surface 3130 rolls along a radially outer surface 3140 of an incoming tape winding 325.

FIG. 32 illustrates how tension in the production line can be maintained within predetermined tolerances. FIG. 32 illustrates the reel 305 and corresponding rim drive 307 illustrated in FIG. 3 in more detail and illustrates how a light curtain 3200 can be utilised to maintain a speed and tension at a desired level in the manufacturing line.

Table 4 illustrates how certain manufacturing process parameters can be controlled. Likewise Table 5 illustrates how certain alarms can be provided in the system so that an audible and/or visual cue is in initiated when a pre-set level for a particular parameter differs by more than a respective predetermined tolerance level.

TABLE 4

| Inputs | |
|---|---|
| Parameter | Required Sensing Range |
| Consolidation Force Set point | 0-400N |
| Consolidation Temp Set point | 0-700° C. |
| Caterpullar Speed Set point | 0-5.0 m/min |
| Caterpullar Clamping Pressure Set point | To be confirmed after discussions with supplier |
| Winding Rate Set point | 0-5.0 m/min |
| Tape Tension Set point | 10N-200N |

TABLE 5

| Alarms | |
|---|---|
| Parameter | Default Tolerance |
| Consolidation Force | ±3N |
| Consolidation Patch Temp | ±5° C. |
| Consolidation Roller Temp | ±5° C. |
| Caterpullar Speed | ±2% |
| Winding Rate | ±2% |
| Tape Tension | ±3N |

FIG. 33 helps illustrate the inspection station 360 in more detail. The inspection station is fixed in location with respect to a pipe production direction P. As illustrated in FIG. 33 the inspection station 360 includes a support 3300 which supports multiple sensors $3310_{0-x}$. It will be appreciated that the support illustrated in FIG. 33 has a central opening through which the tubular composite layer formed over a liner (not shown) passes during a production run. According to alternatives the sensors and sensor support can be arranged to a side or sides of the tubular layer. Likewise alternatively the support can be bidirectional and can be driven backwards and forwards along a region of the tubular composite layer. The layer inspection station 360 thus includes at least one sensor which is located downstream of an in an in-line configuration with an extrusion station or pultrusion station or deposition station or as illustrated in FIG. 3 a winding station for providing a tubular composite layer over an underlying substantially cylindrical surface via a continuous process.

The inspection station 360 is a non-destructive testing (NDT) station which is able to identify one or more regions in the tubular composite layer where a defect may have occurred during a consolidation/manufacturing process. Aptly the NDT station 360 is placed directly after the tape consolidation area. The NDT station locates and/or measures and/or defines and/or records surface and/or sub surface flaws/defects. The inspection station 360 is capable of scanning a broad range of pipe diameters at a linear speed of approximately 1 m/min.

Depending upon the sensors used the sensors will detect conditions which cause attenuation or generate relevant intermediate echoes from an ultrasonic signal or other such probe signal. Aptly these conditions may be one or more of the following occurring during production: longitudinal delamination/voids and/or circumferential delamination/voids and/or local porosity in CFRP tape and/or porosity in tape-tape interfaces and/or surface/thickness profiling. Additionally techniques and sensors can be provided to help identify defects and damage caused by handling and pipe winding such as crush/impact damage and/or delamination at CFRP-liner interface and/or delamination at tape-tape interfaces and/or resin matrix micro cracking. Production tolerances can be pre-set using electronic gates. Triggering of these gates activates an audible and/or visual cue which is relayed to the control station 380.

The sensors 3310 illustrated in FIG. 33 are ultrasonic non-destructive testing sensors. Such ultrasonic testing (UT) sensors can be used to determine a thickness of material and determine a location of a discontinuity within a part of the tubular layer. A discontinuity can be indicative of a defect. Aptly the sensors operate in the range of 500 kHz to 20 MHz. Aptly the sensors use pulse echo testing methods using single crystal probes or groups of single crystal probes or a phased array. The sensors thus send a pulse of ultrasound into a composite part proximate to where the sensor is located. A signal from a far side of the laminate material (referred to as a backwall echo) and other echoes that may be reflected from defects (referred to as an intermediate echo) are detected and measured.

FIG. 34 illustrates an optional test using ultrasonic pulse testing to produce an amplitude trace referred to as an "A-scan". FIG. 34 helps illustrate a backwall echo 3400 reflected from a far side of a laminate that is correctly manufactured. As the sensor 3310 moves with respect to the tubular composite layer (shown in FIG. 35 by relative motion of the sensor 3310 into the middle of the figure where a defect 3500 is located) a pulse echo reflection from such a void shows production of an intermediate echo 3500 and loss of a backwall echo.

FIG. 36 illustrates an alternative defect 3600 which is a relatively small void 3600 smaller in size than an associated transducer diameter. As a result a reduced intermediate echo 3610 and a reduced backwall echo signal 3620 are detected. The detected intermediate and backwall echoes or absences of them and timings with respect to initial pulses can be used to determine a size and nature of a defect.

FIG. 37 helps illustrate how UT sensors 3310 can be utilised to detect a location of porous regions 3700 in a defective region d1 of a tubular composite layer. Regions of porosity are determined by detecting scattered echoes 3700 of an initial pulse from one or more porous regions together with a reduced backwall echo signal 3710.

Optionally B-scan pulse echo tests which show backwall echo reflected from a far side of a tubular composite layer can be utilised. B-scan inspection provides coverage along a desired length of pipe. Adequate coverage around a pipe circumference can be provided by use of multiple probes or by mechanical translation of the probes as the tubular composite layer is manufactured. As illustrated in FIG. 33 two sets of four sensors can be utilised to monitor for a pipe condition. Effectively this produces information indicating regions of the tubular composite layer where a defect has occurred. Aptly outputs from the multiple sensors which each provide a respective probe are multiplexed to provide for real-time monitoring of the tubular composite layer. This permits backwall echo, wall thickness and B-scan data or other such probing parameters for each channel to be recorded and analysed in real time. Aptly ultrasonic data is collected and made available on the display of the control station 380. Production tolerances can be pre-set and triggering at pre-set levels can activate an alarm if a determine defect has characteristics making it too significant to ignore. Aptly a portable phased array equipment is utilised to perform localised inspections of pipe off-line in addition to a main NDT inspection process.

Table 6 illustrates some of the defect types which can optionally be detected and minimum sizes which can be accommodated. Minimum defect size is stated in Table 6 in terms of linear length (L) along the pipe and a fraction of the pipe circumference (C).

TABLE 6

| Type of Indication and Cause | Min Defect Size L × C | Detection Method | Limitations |
|---|---|---|---|
| Void caused by lack of fusion between successive tape layers | 50 mm × 0.25 C | Detection of intermediate echo and/or loss of backwall echo | Narrow linear indications may not be detected if they are less than 25% of pipe circumference |
| Void caused by irregular consolidation around pipe circumference | 50 mm × 0.25 C | Detection of intermediate echo and/or loss of backwall echo | Narrow linear indications may not be detected if they are less than 25% of pipe circumference |
| Clusters of small voids | 50 mm × 0.25 C | Detection of intermediate echo and/or reduction in backwall echo | Cluster analysis required relating number of individual small voids and spacing between them |
| Porosity caused by local porosity in raw tape product | 50 mm × 0.25 C. | Reduction in backwall echo of 75% (12 dB). | Relationship between backwall echo, void content and MKDF needs to be established |
| Porosity caused by poor consolidation between successive tape layers | 5 mm × 0.25 C | Reduction in backwall echo of 75% (12 dB). | Relationship between backwall echo, void content and MKDF needs to be established |

TABLE 6-continued

| Type of Indication and Cause | Min Defect Size L × C | Detection Method | Limitations |
|---|---|---|---|
| Increase in thickness caused by resin richness, under consolidation, over thick tape | More than +10% of nominal thickness | Detection of backwall echo position | Effect of liner velocity and thickness needs to accounted for |
| Reduction in thickness caused by resin starvation, over consolidation, over thin tape | More than −10% of nominal thickness | Detection of backwall echo position | Effect of liner velocity and thickness needs to accounted for |

Aptly further details of the NDT system are set out in Table 7.

Software for the NDT system is provided which can include one or more of the following functions: B-scan cross-section data function of probe position and/or gating of A-scan data to produce backwall echo amplitude and thickness profiles and/or sizing tools with geometry correction and/or charting tools showing indications as a function of pipe length.

TABLE 7

NDT Station Configuration Summary

| Parameter | Details |
|---|---|
| No. of Probes | 4 (Expandable up to 64) |
| No. of Channels | 4 (Expandable up to 64) |
| Probe Diameter | 12 mm |
| Probe Frequency | 1 MHz |
| Coupling Agent | Water bubbler/nylon delay line |
| Probe Standoff | 25 mm |
| Max prf rate | 20 KHz |

FIG. 38 illustrates a repair station 370 in more detail. The repair station 370 is an example of a post process heating and/or cooling station if heating and/or cooling elements are provided. The repair station 370 is in-line and downstream of the inspection station 360 and receives as input and output from a preceding inspection station which provides a location and/or size and/or type of defect at one or more regions of the consolidated tubular composite layer. Should the UT scan from an inspection station 360 identify an area of the tubular composite layer which has not met a predetermined quality then immediate remedial action can be carried out by the repair station 370 without stopping a manufacturing process. Aptly the repair station 370 is placed within 100 meters of an NDT inspection station. Aptly the repair station 370 is placed immediately after an NDT inspection station (within 10 meters). Should the NDT scan identify an area of pipe which has failed to meet a quality required a gated alarm will initiate a procedure within the repair station 270 to locate and repair either surface or sub surface defect. The repair station 370 is capable of carrying out remedial work in real time on a broad range of pipe diameters and at a range of linear speeds of production. Aptly the repair station 370 is able to repair one or more defects simultaneously as a line speed of about around 1 m/min. As illustrated in FIG. 38 the liner 105 and surrounding consolidated layer 110 which provides a tubular composite layer formed by consolidating adjacent windings of tape passes through a central orifice 3800 in a support 3810. The support 3810 supports multiple moveable platens 3820 which are arranged circumferentially around the central circular opening 3800. The support supports the moveable abutment elements 3820 in a manner which allows each abutment element 3820 to be independently moveable along a respective drive axis. This is illustrated more clearly in FIG. 39. As illustrated in FIG. 39 a centre point C is associated with the central opening 3800 in the support 3810. This centre point also corresponds with a central longitudinal axis of the liner 105 and consolidated composite layer 110. This centre point C is common to the drive axis $3900_{0-15}$ for the sixteen abutment elements 3820 illustrated in FIGS. 38 and 39. It will be appreciated that alternatively one, two or more abutment elements can be utilised. Utilising many (for example sixteen shown in FIG. 39) abutment elements means that many locations on an outer surface of the composite layer can be pressurised and/or heated and/or cooled simultaneously. Fewer abutment elements can be utilised and optionally the support 3810 can be rotated by a driving mechanism (not shown) to help align abutment elements with defective regions of the tubular composite layer. Aptly in order to carry out corrective work, heat in the region of between 180° C. to 220° C., and a pressure of up to 4 MPa, can be applied for up to 1 to 2 seconds, locally to a defective region. To help ensure a bond between layers stays intact such pressure and heat is applied. Heat and/or pressure can be applied through the abutment elements 3820 using conduction to transmit the heat, or the heating can be applied separately with focused beams of energy (induction, convection, radiation) immediately prior to the abutment element applying pressure to the area. Aptly the temperature is measured and controlled using temperature sensors (optical pyrometers or the like) or a commercial optical temperature measurement system such as a thermographic imaging camera (e.g. Fluke TiR29 or the like). Aptly pressure can be applied through the abutment elements using hydraulic or pneumatic actuators. To help ensure layers stay intact overheating of tape during the post process heating can be avoided by providing cooling to a treated area immediately after treatment. Cooling to any desired region can be provided to reduce the temperature of that region to a temperature of about around 100° C. rapidly. Cooling can optionally be provided by additional cooling platens (conduction) or by directed cooling air currents (convection).

The abutment elements shown as platens 3820 in FIG. 39 could alternatively be rollers or have other shapes. An abutment surface 3930 is provided on each platen. The abutment surface 3930 illustrated in FIGS. 38 and 39 is convex. Alternatively other shapes such as concave shapes or figure of eight shapes can be utilised. The abutment surface can be urged against outward surface of the composite tape layer for a predetermined period of time and at a desired pressure and temperature to help consolidate porous regions or delaminated regions at locations previously determined in real time by the upstream inspection station.

Aptly thermal energy can be applied via various techniques to the surface or internally or by conduction or by convection and/or by radiation to regions of the pipe. Parameters such as cycle times and/or peak temperature and/or pressure/force application can be likewise applied.

The heating module provides real time information so that trends and failures can be recognised during and after post process heating. This helps support preventative strategies.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. Apparatus for manufacturing a composite layer of a flexible pipe, comprising:
    a layer inspection station comprising at least one sensor, located downstream of and in an in-line configuration with an extrusion station or pultrusion station or winding station or deposition station for providing a tubular composite layer over an underlying substantially cylindrical surface via a continuous process; wherein
    the inspection station automatically and continuously determines if at least one parameter of the tubular composite layer satisfies a respective predetermined condition in at least one region of the tubular composite layer as the tubular composite layer is transported proximate to the inspection station and indicates in real time at least one of a type, size and/or location of a defect in the tubular composite layer; and
    a repair station comprising at least one heater member and/or pressure applicator located downstream of, and in an in-line configuration with, the inspection station for selectively applying a repair cycle by applying a desired temperature and/or pressure at said at least one region.

2. The apparatus as claimed in claim 1, further comprising:
    the inspection station is downstream of, and in-line with, a winding station that comprises a winding carousel for continuously winding at least one tape element helically around the underlying cylindrical surface as a tubular element comprising the cylindrical surface is transported in a first direction of travel.

3. The apparatus as claimed in claim 2, further comprising:
    a tape consolidation station downstream of, and in an in-line configuration with, the winding carousel for consolidating wound tape into a continuous composite layer that comprises said tubular composite layer.

4. The apparatus as claimed in claim 1, further comprising:
    the inspection station is located within 100 linear pipe meters of a touch down position where extruded material contacts the underlying cylindrical surface or where tape is wound onto the cylindrical surface respectively.

5. The apparatus as claimed in claim 1, further comprising:
    the at least one sensor comprises at least one ultra-sonic sensor.

6. The apparatus as claimed in claim 1, further comprising:
    the at least one sensor indicates surface and sub-surface defects in the tubular composite layer.

7. The apparatus as claimed in claim 1, further comprising:
    the at least one sensor of the inspection station comprises a plurality of sensors disposed in a spaced apart relationship circumferentially around an outer surface of the tubular composite layer at a common location with respect to a longitudinal axis associated with a travel path of the tubular composite layer.

8. The apparatus as claimed in claim 7, further comprising:
    an output from each sensor is connected to an analysis unit via a multiplexor element for providing real-time monitoring of the at least one parameter at multiple regions of the tubular composite layer.

9. The apparatus as claimed in claim 1, further comprising:
    the repair station selectively heats the at least one tubular composite layer region to about around 120° C. to 250° C.

10. The apparatus as claimed in claim 1, further comprising:
    the repair station selectively applies a pressure of about around 0.5 to 4 MPa via the heating member and/or pressure applicator to the at least one tubular composite layer region.

11. The apparatus as claimed in claim 1, further comprising:
    the repair station selectively applies the desired temperature and/or pressure for about around 0.5 to 60 seconds.

12. The apparatus as claimed in claim 11 wherein the temperature and/or pressure is applied for about around 1 to 2 seconds.

13. The apparatus as claimed in claim 1, further comprising:
    the repair station comprises at least one heater element.

14. The apparatus as claimed in claim 13 wherein the heater element comprises at least one of an infrared heater or induction heater or conductive heater or resistive heater.

15. The apparatus as claimed in claim 1, further comprising:
    the repair station comprises at least one cooler element which optionally comprises a fan element.

16. The apparatus as claimed in claim 1, further comprising:
the repair station comprises at least one pressure applying member having an abutment surface having a shape at least substantially corresponding to a shape of an outer surface of the tubular composite layer or that is convex or concave.

17. The apparatus as claimed in claim 2, further comprising:
at least one tape spool that provides windable tape to the winding carousel for winding over the tubular element.

18. The apparatus as claimed in claim 17, further comprising:
a consolidation station located downstream of and in an in-line configuration with the winding station and upstream of, and in an in-line configuration with, the inspection station.

19. A method of manufacturing a composite layer of a flexible pipe, comprising the steps of:

via at least one sensor at a layer inspection station downstream of, and in an in-line configuration with, an extrusion station or pultrusion station or winding station or deposition station, automatically and continuously determining if at least one parameter of a tubular composite layer satisfies a respective predetermined condition in at least one region of the tubular composite layer and indicating in real time at least one of a type, size and/or location of a defect in the tubular composite layer; and responsive to detection of a defect in at least one region via the inspection station, via a repair station located downstream of, and in an in-line configuration with the inspection station, selectively applying a desired fixed or varying temperature and/or pressure to a defective region as the defective region is transported proximate to the repair station.

* * * * *